(12) United States Patent
Van Leeuwen et al.

(10) Patent No.: US 8,987,203 B2
(45) Date of Patent: Mar. 24, 2015

(54) METHODS FOR CONTROLLING MINERALIZATION OF EXTRACELLULAR MATRIX, THERAPEUTIC METHODS BASED THEREON AND MEDICAMENTS FOR USE THEREIN

(75) Inventors: Johannes Petrus Thomas Maria Van Leeuwen, Amstelveen (NL); Hermanus Johannes Marco Eijken, Rotterdam (NL)

(73) Assignee: Arcarios B.V., Rotterdam (NL)

( * ) Notice: Subject to any disclaimer, the term of this patent is extended or adjusted under 35 U.S.C. 154(b) by 986 days.

(21) Appl. No.: 12/515,202

(22) PCT Filed: Nov. 16, 2007

(86) PCT No.: PCT/NL2007/050571
§ 371 (c)(1),
(2), (4) Date: Dec. 9, 2009

(87) PCT Pub. No.: WO2008/060156
PCT Pub. Date: May 22, 2008

(65) Prior Publication Data
US 2010/0113327 A1    May 6, 2010

(30) Foreign Application Priority Data

Nov. 17, 2006 (WO) ................ PCT/NL2006/000576

(51) Int. Cl.
| | |
|---|---|
| *A61K 38/00* | (2006.01) |
| *A61P 19/08* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C12N 5/077* | (2010.01) |
| *A61K 38/17* | (2006.01) |

(52) U.S. Cl.
CPC .............. *C12N 5/0654* (2013.01); *A61K 38/17* (2013.01); *C12N 2501/16* (2013.01)
USPC .......................................... 514/16.7; 530/300

(58) Field of Classification Search
None
See application file for complete search history.

(56) References Cited

U.S. PATENT DOCUMENTS

| | | | |
|---|---|---|---|
| 4,448,889 A | 5/1984 | Neri et al. | |
| 4,871,678 A | 10/1989 | Wahl et al. | |
| 2003/0144203 A1* | 7/2003 | Bowen | 514/12 |
| 2004/0176287 A1* | 9/2004 | Harrison et al. | 514/12 |

FOREIGN PATENT DOCUMENTS

| | | |
|---|---|---|
| WO | WO 99/61474 A1 | 12/1999 |
| WO | WO2005/009460 * | 2/2005 |
| WO | WO-2006/119406 | 11/2006 |

OTHER PUBLICATIONS

Tsuchida et al. "Activin signaling as an emerging target for therapeutic interventions" Cell Communication and Signaling 7:15. Published Jun. 18, 2009.*
Eijken et al., Molecular and Cellular Endocrinology (2006) 248:87-93.
Hashimoto et al., Journal of Biological Chemistry (1992) 267(7):4999-5004.
Hirotani et al., Calcified Tissue International (2002) 70(4):330-338.
Ikenoue et al., Journal of Cellular Biochemistry (1999) 75(2):206-214.
International Search Report for PCT/NL2007/050571, mailed on Apr. 9, 2008, 5 pages.
Kitamura et al., Journal of Hepatology (2005) 42:11 abstract 23.
Sakai et al., Bone (1999) 25(2):191-196.
Sakai et al., Bone (2000) 27:91-96.
Werner et al., Cytokine and Growth Factor Reviews (2006) 17(3):157-171.
Abedin, et al. Vascular calcification: mechanisms and clinical ramifications. Arterioscler Thromb Vasc Biol. Jul. 2004;24(7):1161-70. Epub May 20, 2004.
Alliston, et al. TGF-beta-induced repression of CBFA1 by Smad3 decreases cbfa1 and osteocalcin expression and inhibits osteoblast differentiation. EMBO J. May 1, 2001;20(9):2254-72.
Beck, et al. Inorganic phosphate regulates multiple genes during osteoblast differentiation, including Nrf2. Exp Cell Res. Aug. 15, 2003;288(2):288-300.
Bilezikjian, et al. Autocrine/paracrine regulation of pituitary function by activin, inhibin and follistatin. Mol Cell Endocrinol. Oct. 15, 2004;225(1-2):29-36.
Canalis, et al. Bone morphogenetic proteins, their antagonists, and the skeleton. Endocr Rev. Apr. 2003;24(2):218-35.
Centrella, et al. Activin-A binding and biochemical effects in osteoblast-enriched cultures from fetal-rat parietal bone. Mol Cell Biol. Jan. 1991;11(1):250-8.

(Continued)

*Primary Examiner* — James H Alstrum Acevedo
*Assistant Examiner* — Zachary J Miknis
(74) *Attorney, Agent, or Firm* — Wilson, Sonsini, Goodrich & Rosati, PC

(57) ABSTRACT

The present invention relates to methods for selecting a candidate therapeutic agent for controlling mineralization of an extracellular matrix in a tissue of a subject. The invention further relates to a cell culture mineralization model comprising a culture of an extracellular matrix producing cell under conditions that support extracellular matrix formation and matrix maturation, a test compound, and means and methods for determining in expression levels of genes encoding matrix proteins.

6 Claims, 9 Drawing Sheets

(56) References Cited

OTHER PUBLICATIONS

Chen, et al. Activin signaling and its role in regulation of cell proliferation, apoptosis, and carcinogenesis. Exp Biol Med (Maywood). May 2006;231(5):534-44.

Dennler, et al. Direct binding of Smad3 and Smad4 to critical TGF beta-inducible elements in the promoter of human plasminogen activator inhibitor-type 1 gene. EMBO J. Jun. 1, 1998;17(11):3091-100.

Eijken, et al. 11beta-Hydroxysteroid dehydrogenase expression and glucocorticoid synthesis are directed by a molecular switch during osteoblast differentiation. Mol Endocrinol. Mar. 2005;19(3):621-31. Epub Dec. 9, 2004.

Eijken, et al. The activin A-follistatin system: potent regulator of human extracellular matrix mineralization. FASEB J. Sep. 2007;21(11):2949-60. Epub Apr. 20, 2007.

El-Abbadi, et al. Arteriosclerosis, calcium phosphate deposition and cardiovascular disease in uremia: current concepts at the bench. Curr Opin Nephrol Hypertens. Nov. 2005;14(6):519-24.

Engelse, et al. Human activin-A is expressed in the atherosclerotic lesion and promotes the contractile phenotype of smooth muscle cells. Circ Res. Nov. 12, 1999;85(10):931-9.

Fainsod, et al. The dorsalizing and neural inducing gene follistatin is an antagonist of BMP-4. Mech Dev. Apr. 1997;63(1):39-50.

Fratzl-Zelman, et al. Matrix mineralization in MC3T3-E1 cell cultures initiated by beta-glycerophosphate pulse. Bone. Dec. 1998;23(6):511-20.

Gaddy-Kurten, et al. Inhibin suppresses and activin stimulates osteoblastogenesis and osteoclastogenesis in murine bone marrow cultures. Endocrinology. Jan. 2002;143(1):74-83.

Govoni, et al. The multi-functional role of insulin-like growth factor binding proteins in bone. Pediatr Nephrol. Mar. 2005;20(3):261-8. Epub Nov. 11, 2004.

Guo, et al. Overexpression of mouse follistatin causes reproductive defects in transgenic mice. Mol Endocrinol. Jan. 1998;12(1):96-106.

Harris, et al. Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts. J Bone Miner Res. Jun. 1994;9(6):855-63.

Harrison, et al. Antagonists of activin signaling: mechanisms and potential biological applications. Trends Endocrinol Metab. Mar. 2005;16(2):73-8.

Ichida, et al. Reciprocal roles of MSX2 in regulation of osteoblast and adipocyte differentiation. J Biol Chem. Aug. 6, 2004;279(32):34015-22. Epub Jun. 1, 2004.

Iemura, et al. Direct binding of follistatin to a complex of bone-morphogenetic protein and its receptor inhibits ventral and epidermal cell fates in early *Xenopus* embryo. Proc Natl Acad Sci U S A. Aug. 4, 1998;95(16):9337-42.

Itoh, et al. Signaling of transforming growth factor-beta family members through Smad proteins. Eur J Biochem. Dec. 2000;267(24):6954-67.

Janssens, et al. Transforming growth factor-beta1 to the bone. Endocr Rev. Oct. 2005;26(6):743-74. Epub May 18, 2005.

Kanzaki, et al. Production of activin A and follistatin in cultured rat vascular smooth muscle cells. Mol Cell Endocrinol. Feb. 27, 1995;108(1-2):11-6.

Korchynskyi, et al. Identification and functional characterization of distinct critically important bone morphogenetic protein-specific response elements in the Id1 promoter. J Biol Chem. Feb. 15, 2002;277(7):4883-91. Epub Nov. 29, 2001.

Lewis, et al. Betaglycan binds inhibin and can mediate functional antagonism of activin signalling. Nature. Mar. 23, 2000;404(6776):411-4.

Maeda, et al. Endogenous TGF-beta signaling suppresses maturation of osteoblastic mesenchymal cells. EMBO J. Feb. 11, 2004;23(3):552-63. Epub Jan. 29, 2004.

Martens, et al. Inhibin interferes with activin signaling at the level of the activin receptor complex in Chinese hamster ovary cells. Endocrinology. Jul. 1997;138(7):2928-36.

Matzuk, et al. Functional analysis of activins during mammalian development. Nature. Mar. 23, 1995;374(6520):354-6.

Matzuk, et al. Multiple defects and perinatal death in mice deficient in follistatin. Nature. Mar. 23, 1995;374(6520):360-3.

Nakamura, et al. Activin-binding protein from rat ovary is follistatin. Science. Feb. 16, 2000;247(4944):836-8.

Ogawa, et al. Bovine bone activin enhances bone morphogenetic protein-induced ectopic bone formation. J Biol Chem. Jul. 15, 1992;267(20):14233-7.

Oreffo, et al. Activation of the bone-derived latent TGF beta complex by isolated osteoclasts. Biochem Biophys Res Commun. Feb. 15, 1989;158(3):817-23.

Oshima, et al. A novel mechanism for the regulation of osteoblast differentiation: transcription of periostin, a member of the fasciclin I family, is regulated by the bHLH transcription factor, twist. J Cell Biochem. 2002;86(4):792-804.

Oursler. Osteoclast synthesis and secretion and activation of latent transforming growth factor beta. J Bone Miner Res. Apr. 1994;9(4):443-52.

Pierre, et al. Testing the antagonistic effect of follistatin on BMP family members in ovine granulosa cells. Reprod Nutr Dev. Jul.-Aug. 2005;45(4):419-25.

Raggi, et al. Identification of patients at increased risk of first unheralded acute myocardial infarction by electron-beam computed tomography. Circulation. Feb. 29, 2000;101(8):850-5.

Robey, et al. Extracelluar matrix and biomineralization of bone. Murray, J. F. eds. Primer on the Metabolic Bone Diseases and Disorders of Mineral Metabolism The American Society for Bone and Mineral Research Washington, D.C. 2006.

Sakai, et al. Activin enhances osteoclast-like cell formation in vitro. Biochem Biophys Res Commun. Aug. 31, 1993;195(1):39-46.

Sakai, et al. Involvement of activin in the regulation of bone metabolism. Mol Cell Endocrinol. Jun. 30, 2001;180(1-2):183-8.

Schubert, et al. Activin is a nerve cell survival molecule. Nature. Apr. 26, 1990;344(6269):868-70.

Seeman, et al. Bone quality—the material and structural basis of bone strength and fragility. N Engl J Med. May 25, 2006;354(21):2250-61.

Shao, et al. Msx2 promotes cardiovascular calcification by activating paracrine Wnt signals. J Clin Invest. May 2005;115(5):1210-20. Epub Apr. 14, 2005.

Shioi, et al. Beta-glycerophosphate accelerates calcification in cultured bovine vascular smooth muscle cells. Arterioscler Thromb Vasc Biol. Nov. 1995;15(11):2003-9.

Spencer, et al. Activin and inhibin in the human adrenal gland. Regulation and differential effects in fetal and adult cells. Clin Invest. Jul. 1992;90(1):142-9.

Steitz, et al. Smooth muscle cell phenotypic transition associated with calcification: upregulation of Cbfa1 and downregulation of smooth muscle lineage markers. Circ Res. Dec. 7, 2001;89(12):1147-54.

Tenenbaum, et al. Chondroitin sulfate inhibits calcification of bone formed in vitro. Bone Miner. Feb. 1987;2(1):43-51.

Wain, et al. Guidelines for human gene nomenclature. Genomics. Apr. 2002;79(4):464-70.

Watson, et al. TGF-beta 1 and 25-hydroxycholesterol stimulate osteoblast-like vascular cells to calcify. J Clin Invest. May 1994;93(5):2106-13.

Wewer, et al. A potential role for tetranectin in mineralization during osteogenesis. J Cell Biol. Dec. 1994;127(6 Pt 1):1767-75.

Xu, et al. Inhibin antagonizes inhibition of liver cell growth by activin by a dominant-negative mechanism. J Biol Chem. Mar. 17, 1995;270(11):6308-13.

Young, et al. OntologyTraverser: an R package for GO analysis. Bioinformatics. Jan. 15, 2005;21(2):275-6. Epub Aug. 27, 2004.

Zhang, et al. Inhibition of activin signaling induces pancreatic epithelial cell expansion and diminishes terminal differentiation of pancreatic beta-cells. Diabetes. Aug. 2004;53(8):2024-33.

* cited by examiner

METHODS FOR CONTROLLING MINERALIZATION OF EXTRACELLULAR MATRIX, THERAPEUTIC METHODS BASED THEREON AND MEDICAMENTS FOR USE THEREIN

CROSS-REFERENCE TO RELATED APPLICATIONS

This application is the national phase of PCT application PCT/NL2007/050571 having an international filing date of 16 Nov. 2007, which claims benefit of PCT application No. PCT/NL2006/000576 filed 17 Nov. 2006. The contents of the above patent applications are incorporated by reference herein in their entirety.

FIELD OF THE INVENTION

The present invention relates to methods for selecting biologically active compounds that control bone mineralization. In particular the present invention relates to methods for selecting a candidate therapeutic agent for controlling mineralization of an extracellular matrix in a tissue of a subject, and to methods for controlling the mineralization of an extracellular matrix, especially as associated with bone forming cells and/or vascular smooth muscle cells and/or other ectopic, pathological calcifications. The invention further relates to a cell culture mineralization model comprising a culture of an extracellular matrix producing cell under conditions that support extracellular matrix formation and matrix maturation, a test compound, and means and methods for determining in expression levels of genes encoding matrix proteins. The present invention also relates to methods of treatment and to medicaments for use in such treatment methods.

BACKGROUND TO THE INVENTION

Osteoporosis is a disease in which the density and quality of bone are reduced, leading to weakness of the skeleton and increased risk of fracture, particularly of the spine, wrist, hip, pelvis and upper arm. Osteoporosis and associated fractures are an important cause of mortality and morbidity. Bone quality is a crucial feature in osteoporosis and osteoblasts play a pivotal role as the bone forming cell and the director of bone resorption by osteoclasts. Osteoblasts have a meschenchymal origin and the differentiation of mesenchymal stem cells to an osteoblastic lineage is regulated by many endocrine, paracrine and autocrine factors. During bone formation osteoblasts produce an organic extracellular matrix (ECM) or osteoid (the immature matrix before mineralizing), which is composed primarily of type I collagen and non-collagenous proteins. This ECM then mineralizes, by the deposition thereon of calcium phosphates, to form bone spicules. Initiation of bone mineralization, or ossification, requires the precipitation and attachment of calcium phosphate crystals, in particular hydroxyapatite ($Ca_{10}(PO_4)_6(OH)_2$), to the ECM.

This process of mineralization is not unique for bone cells. It also occurs in hypertrophic chondrocytes as part of endochondral bone formation during growth. Furthermore, in pathological conditions of vascular calcification, mineralization of vascular smooth muscle cell (VSMC) ECM is believed to be involved in vascular calcification as well as in calcification of articular cartilage which occurs with ageing, degenerative joint diseases (e.g. osteoarthritis), and various metabolic and genetic disorders. Thus, ECM mineralization is a physiological process in bone and a pathological one in soft tissues.

Bone mineralization and in particular its regulation is a complicated process controlled by many factors including serum calcium and phosphate concentrations, hormones, enzymes, and the structure of the ECM. The macromolecular organization of type I collagen is a factor facilitating bone mineralization. Initially, calcium phosphate is deposited in the holes of the collagen fibrils and later fills in the pores and the rest of the space within the collagen fibrils.

Vascular calcification, and particular arterial calcification, has long been considered a passive process involving the necrotic core of the plaque serving as a nucleating centre for calcium phosphate mineral deposition. Recent scientific insights have challenged this hypothesis in that genetic aberrations of a variety of extracellular matrix (ECM) molecules, including matrix Gla protein and osteoprotegerin, result in spontaneous arterial calcification, indicating that like bone mineralization, arterial calcification is a delicately regulated process.

It is evident that the possibility of controlling the ECM mineralization process is desired, both in the direction of promoting mineralization as in the case of osteoporosis and fracture healing, and in the case of reducing or preventing mineralization as in the case of vascular calcification, in particular atherosclerotic calcification, and calcification of cartilage.

It is an aim of the present invention to provide methods for selecting candidate therapeutic agents for controlling mineralization of an extracellular matrix in a tissue of a subject, preferably in a mammal, most preferably a human. It is another aim of the present invention to provide methods for controlling ECM mineralization in soft tissue of a mammal, preferably a human, particularly in relation to pathological calcification of cartilage and blood vessels, such as mineralization of VSMC produced ECM and atherosclerosis. It is still another aim of the invention to provide methods of control by providing possibilities to stimulate mineralization on the one hand, and by providing possibilities to reduce or prevent mineralization on the other. It is a further aim to provide pharmaceutical compositions and medicaments for use in such methods.

SUMMARY OF THE INVENTION

In a first aspect, the present invention provides a method for selecting a candidate therapeutic agent for controlling mineralization of an extracellular matrix in a tissue of a subject, said method comprising the steps of:
  a) exposing a cell from said tissue that produces an extracellular matrix to a test compound under conditions that support extracellular matrix formation and matrix maturation;
  b) determining the expression in said cell of at least one gene in response to said exposure, wherein said gene is selected from
    group A consisting of genes that encode for thrombospondin 1; collagen type V alpha 1; collagen type XVI alpha 1; collagen type VIII alpha 2; collagen triple helix repeat containing 1; hyaluronan and proteoglycan link protein 1; chondroitin sulfate proteoglycan 2 (versican); latent transforming growth factor beta binding protein 2; biglycan; matrix metallopeptidase 2; periostin, osteoblast specific factor; fibulin 5; SPOCK1, Sparc/osteonectin, cwcv and kazal-like domains proteoglycan (testican); and ADAM metallopeptidase with thrombospondin type 1 motif; and/or group B consisting of genes that encode for CD248 antigen, endosialin; elastin microfibril interfacer 2; matrilin 2; dystrobrevin, alpha; collagen, type IV, alpha 6; nidogen 2 (osteonidogen); papilin, proteoglycon-like sulfated glycoprotein; C-type lectin domain family 3, member B; collagen type V, alpha 3; and TIMP metallopetidase inhibitor 4; and c) selecting said test compound as a candidate therapeutic agent for controlling mineralization of an extracellular matrix in a tissue of a subject in case the expression of said at least one gene in said cell is regulated as a direct result of said exposure.

The step of exposing an extracellular matrix-producing cell from the tissue to a test compound is preformed for a period of time that is effective to exert a response (i.e. from a few hours to several days or more) on the cellular gene expression. As the genetic repertoire of the cell is also influenced by other external conditions, the cell should be placed under conditions that support extracellular matrix formation and matrix maturation in the presence of the test compound.

The step of determining the expression in the cell of at least one gene may suitably comprise the determination of the expression level of two genes, more preferably 3, 4, 5, 6, 7, 8, 9, 10, 11, 12, 13, 14, 15, 16, 17, 18, 19, 20, 21, 22, 23 or 24 genes selected from group A and B as defined above. More preferably an increase or decrease in the expression level of at least one gene of group A is determined in combination with a concomitant decrease or increase (that is reverse) in the expression level of at least one gene of group B. In a most preferred embodiment an increase or decrease in the expression level of essentially all group A genes is determined in combination with a concomitant decrease or increase in the expression level of essentially all group B genes. Thus, most preferably the relative expression of group A genes is determined in relation to the expression of group B genes, wherein the test compound is identified as a candidate therapeutic agent for controlling mineralization in case a relative downregulation of group A genes coincides with a relative upregulation of group B genes, or vice versa, depending on whether the agent is effective in inhibiting or stimulating matrix maturation and subsequent mineralization.

The above method for selecting candidate therapeutic agents is suitably exemplified in a cell culture model for the screening of therapeutic efficacy of a compound on mineralization (a mineralization-model). This cell culture model is essentially a culture of cells that produce an extracellular matrix, which matrix can be mineralized by virtue of calcium phosphate deposition. The inventors have discovered that the mineralization of the matrix of for instance human osteoblasts or mesenchymal stem cells need not fully mineralize before one can determine the effect of the compound on the mineralization potential of the matrix. The mineralization model is based on the insight that activin signalling results in blockage of the development of the matrix towards a mature (mineralizable or pre-mineralized) state, which state is defined by a certain composition of matrix proteins. The blockage of the development of the matrix is the result of gene expression regulation of matrix proteins. Thus, by measuring the effect on the gene expression level of specific matrix proteins, preferably the upregulation of certain genes and the downregulation of others, in particular between the groupings A and B as defined herein, the potential of a test compound to exert an (therapeutic) effect on mineralization (or the prevention thereof) can be evaluated, and the test compound can be identified as a candidate therapeutic agent and eventually selected by making it available for that therapeutic purpose.

It is an embodiment of aspects of the present invention that the culture of cells that produce an extracellular matrix, may comprise cells of knockout cell lines, wherein one or more genes involved in the activin signalling cascade or involved in matrix maturation (e.g. that encode matrix proteins or transcription factors involved in matrix maturation) are knocked out, for instance by using siRNA approaches well known in the art. Such cell lines can form the basis of an appropriate model system for various mineralization disorders, and may be used to discover and ultimately select compounds that neutralize or ameliorate the disorder, or identify appropriate therapeutic targets for treating such disorders.

The validity of the models was demonstrated by activin-A which inhibited mineralization, and follistatin, which could neutralize the effect of activin A. Thus, the present invention provides for a much improved screening method for candidate therapeutic agents based on cell culture mineralization models wherein matrix-protein expression is determined. Preferred models are illustrated in the Examples below.

The cell culture mineralization model comprises essentially i) a culture of an extracellular matrix producing cell under conditions that support extracellular matrix formation and matrix maturation, ii) a test compound, and iii) means and methods for determining the expression level in that cell of the group A and/or group B genes as defined above as a result of exposure of the cells in said culture to said test compound. The operation of the model, which model may take the form of a kit-of-parts, involves adding a test compound to the cell culture medium thereby exposing said cell to said test compound, allowing the exposure to continue for the duration of the pre-mineralization period, and determining the expression level of at least one gene of group A and/or group B as defined above in that cell, wherein a regulation of the expression as a result of the exposure, preferably a specific up- and down-regulation of particular gene expressions as described below, is indicative of the potential of the test compound to be a candidate therapeutic agent for controlling mineralization of an extracellular matrix in a tissue of a subject.

In a method of the present invention, the expression of said at least one gene may be determined by any means to measure the mRNA levels transcribed from said at least one gene, or by protein analysis of said cell or said extracellular matrix. The means and methods for determining in that cell the expression level of the group A and/or group B genes as described above suitable involve a nucleic acid array (gene chip array) and hybridization protocols for determining gene expression levels in a tissue cell. Such hybridization protocols are well known in the art and generally involve reverse transcription of mRNA into cDNA, amplification of the obtained cDNA in the presence of nucleotides labelled with a detectable label to produce labelled cDNA amplification product, hybridization of the labelled cDNA to nucleic acids on the nucleic acid array under stringent hybridization conditions, removal of non-hybridized product and detection of hybridization on the array by detection of the label.

In one particularly preferred embodiment of a method of the present invention for selecting a candidate therapeutic agent for controlling mineralization, the agent is for stimulating mineralization, bone healing, bone formation and/or for treating osteoporosis. In such a method, the cell is preferably an osteoblast. In a further embodiment of such a method the test compound is identified as a candidate therapeutic agent for stimulating mineralization, bone healing, bone formation and/or for treating osteoporosis when at least one gene of group A as defined herein is down-regulated and/or at least one gene of group B as defined herein is up-regulated. The method may suitably be performed by using any compound, preferably functional analogues of follistatin, activin A-inhibitors, inducers of activin A-inhibitors and antagonists of the type-II activin receptor as the test compound.

Upon identification of a candidate therapeutic agent according to the invention, one may optionally want to verify the suitability of the agent to control matrix mineralization. Such a verification assay may comprise the steps of continuing the exposure of the cultured cells to the candidate therapeutic agent for a length of time past the mature phase of the matrix and into the phase where the matrix development involves calcium phosphate deposition (mineralization). To reach that phase, the exposure is preferably continued for period of more than 12 days (onset mineralization), preferably more than 15 days, more preferably about 19 days, or at least well into the mineralization phase. The assay then involves the measurement of calcium phosphate deposition in said matrix in order to evaluate the true effect of the agent on mineralization. Use can be made of suitable control compounds such as activin A (as a mineralization inhibitor) or follistatin (as an inhibitor of activin A). Assay for measuring calcium phosphate deposition in the matrix are well known in the art and may be based on determination of matrix calcium content. This may occur colorimetrically by using a color reagent for measuring calcium based on ortho-cresolphthalein complexone (see e.g. U.S. Pat. Nos. 4,448,889 and 4,871,678. Alternatively, one may use Alizarin Red S staining (e.g. as commercially available in the form of an Osteogenesis Quantitation Kit from Millipore Corporation)

In another particularly preferred embodiment of a method of the present invention for selecting a candidate therapeutic agent for controlling mineralization, the agent is for preventing mineralization or for treating calcification disorders. The calcification disorder can for instance be a pathological calcification selected from the group consisting of atherosclerotic calcification, metastatic pulmonary calcification, heart valve calcification, and the calcifications in the joints associated with tendonitis; arthritis; bursitis; bone spurs; cutaneous ossification; kidney stones; myositis ossificans; pulmonary ossification; cataracts; bilateral striopallidodentate calcinosis; neurogenic heterotopic ossification and osteosarcoma. In such a method, the cell is preferably a vascular smooth muscle cell. In a further embodiment of such a method the test compound is identified as a candidate therapeutic agent for preventing mineralization or for treating calcification disorders when at least one gene of group A as defined herein is up-regulated and/or at least one gene of group B as defined herein is down-regulated. The method may suitably be performed by compounds including functional analogues of activin A, an endogenous inducer of activin A and an agonist of the type-II activin receptor.

In another aspect, the present invention provides a therapeutic agent for preventing mineralization or for treating calcification disorders, wherein said candidate therapeutic agent is activin A.

In yet another aspect, the present invention provides a pharmaceutical composition for preventing mineralization or for treating calcification disorders, comprising a therapeutically effective amount of activin A and a pharmaceutically acceptable vehicle.

In still another aspect, the present invention provides a therapeutic agent for stimulating mineralization, bone healing, bone formation and/or for treating osteoporosis, wherein said candidate therapeutic agent is follistatin.

In still a further aspect, the present invention provides a pharmaceutical composition for preventing mineralization or for treating calcification disorders, comprising a therapeutically effective amount of activin A and a pharmaceutically acceptable vehicle.

In a method for treating or preventing pathological calcifications, the cell that produces said extracellular matrix is preferably a vascular cell, more preferably a vascular smooth muscle cell. Alternatively, the cell may be a chondrocyte or the cell driving the pathological calcifications in either one of the following conditions: metastatic pulmonary calcification, heart valve calcification, tendonitis; arthritis; bursitis; bone spurs; cutaneous ossification; kidney stones; myositis ossificans; pulmonary ossification; cataracts; bilateral striopallidodentate calcinosis; neurogenic heterotopic ossification and osteosarcoma.

In yet another aspect, the present invention relates to a method of producing a non-mineralizing extracellular matrix. Such a matrix is essentially produced as part of a tissue (e.g. a collection of similar cells and the intercellular substances surrounding them), and the matrix may optionally be isolated from the tissue, i.a. by the removal of cells. Such a method essentially comprises the culture of a suitable matrix-producing tissue under conditions wherein the cells of said tissue produce an extracellular matrix. According to a method of the invention for producing non-mineralizing matrix, the method is performed in combination with any method of the present invention wherein the maturation and/or mineralization of the matrix is prevented or inhibited.

In yet another aspect, the present invention relates to a method of producing a rapidly-mineralizing extracellular matrix. Such a method is essentially analogous to the one just described for producing the non-mineralizing matrix, but here the method is performed in combination with any method of the present invention wherein the maturation and/or mineralization of the matrix is stimulated.

In yet another aspect, the present invention provides a marker for diagnosing osteoporosis in a subject, wherein said marker is the ratio of the amount of activin-A to the amount of follistatin in a fluid or tissue sample of said subject and wherein said ratio is elevated when compared to control subjects. Suitable fluid samples include blood, serum, urine, saliva, synovial fluid and liquor, and suitable tissue samples include bone and cartilage or other connective tissue, muscle tissue, lipid tissue, bone marrow, blood(-cells), and epithelium of gut or skin.

DETAILED DESCRIPTION OF THE INVENTION

Figure 1:
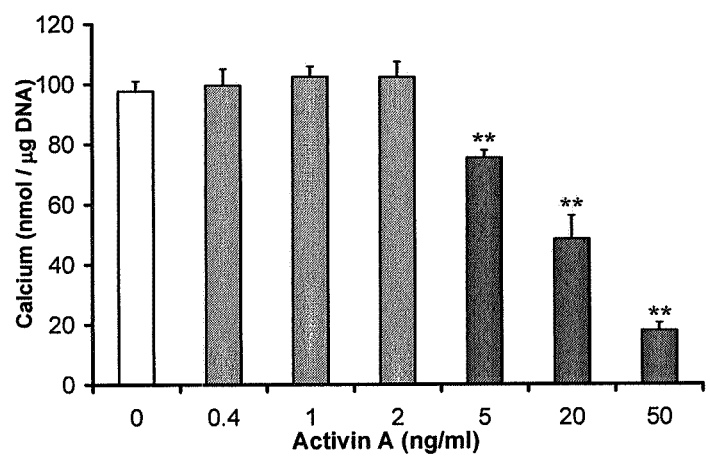
FIG. 1 shows the inhibition of mineralization by activin signaling. Osteoblasts (SV-HFO) were cultured for 19 days in the presence of various concentration of activin-A. Calcium content was quantified at day 19. ** $p<0.01$ compared to vehicle cultures.

In order to provide a clearer and consistent understanding of the specification and claims, including the scope to be given such terms, the following definitions are provided.

The term "extracellular matrix", abbreviated "ECM", refers to the complex structural material that is produced by cells in mammalian tissues, particularly cells of connective tissue, for instance such cells as fibroblasts, osteoblasts, chondrocytes, epithelial cells, smooth muscle cells, adipocytes, and mesenchymal cells, and which material in vivo surrounds and supports those cells. Typically, the ECM is composed of fibres embedded in what is commonly referred to as 'ground substance'. The fibers are composed of structural proteins, generally collagen and/or elastin. In aspects of the present invention, the fibers of the matrix are preferably collagen. Particularly suitable collagens are fibril-forming collagens. Type I collagen, type II collagen, type III collagen, type IV collagen or type X collagen are particularly preferred. Most preferred is type I collagen. The 'ground substance' is composed of proteoglycans (or mucopolysaccharides) and may comprise functionality-providing proteins such as fibrillin, fibronectin, and/or laminin. In aspects of the invention, the ECM suitably comprises at least one proteoglycan as a component of the ground substance. The proteoglycan is composed of a core protein with pending glycosaminoglycan (GAG) molecules. Suitable GAGs are for instance hyaluronic acid, chondroitin-4-sulfate, chondroitin-6-sulphate, dermatan sulphate, heparan sulphate, heparin sulphate, and keratan sulfate. The GAGs are preferably linked to the core protein via a trisaccharide linker (e.g. a GalGalXyl linker). Exemplary proteoglycans are decorin, biglycan, versican and aggrecan. The proteoglycans may optionally be interconnected by hyaluronic acid molecules. Alternatively, multiple proteoglycans may be attached to a single hyaluronic acid backbone. In both cases the ground substance forms a polymer network or gel capable of holding water. The network may further comprise such proteins as: glycoproteins such as laminin, entactin, tenascin fibrillin or fibronectin, for improving structural integrity of the network and for the attachment of cells to the ECM; osteocalcin (Gla protein), as a protein that binds calcium during mineralization; osteonectin, which serves a bridging function between collagen and mineral component; and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE). The matrix may further comprise cytokines and growth factors. Suitable cytokines and growth factors include osteoprotegerin (OPG), epidermal growth factor (EGF), fibroblast growth factors (bFGF, FGF-1, and FGF-2), interferon-α (IFN-α), interleukins (IL-1, IL-4, IL-6, IL-10, and IL-11), platelet-derived growth factor (PDGF), transforming growth factors (TGF-α and TGF-β), tumor necrosis factors (TNFs), insulin-like growth factors (IGF-I and IGF-II), osteoclast differentiation factor (ODF, also known as OPGL [osteoprotegerin ligand], RANKL [receptor activator of NFB ligand], TRANCE [TNF-related activation-induced cytokine]), and macrophage colony-stimulating factor (M-CSF). Most of these (IL-1, IL-4, IL-6, IL-11, TNF, EGF, bFGF, FGF-2, PDGF, and M-CSF) stimulate bone resorption. Some (IGF-I and IGF-II, FGF-2, and TGF-3) enhance bone formation, while others (OPG) inhibit bone resorption. Still others (PDGF and TGF-β) also stimulate proliferation and differentiation of collagen-synthesizing cells. A preferred cytokine is OPG. Preferred growth factors include BMP, IGF, PTH and PDGF. When used in aspects of the present invention, the term "extracellular matrix" refers both to the material in vivo, as well as to the material in isolated form, separated from the cells that produced it. The ECM in aspects of the present invention can be a natural or artificial material (e.g. a proteinaceous or peptide hydrogel).

The term "activin" as used herein, refers to molecules consisting of homodimers of inhibin β subunits linked by a disulfide bond. Several isoform of the β subunit exist, including the most common inhibin-βA and inhibin-βB, creating three isoforms of activin, activin-A (βAβA), activin-B (βBβB) and activin-AB (βAβB). Activins need type I and type II activin-receptors for their signal transduction. Activins binds to type-II activin receptor (ACVR2A/2B), leading to recruitment and phosphorylation of the type-I activin receptor (ACVR1B also known as ALK4). The phosphorylated type-I receptor, in turn, phosphorylates intracellular signaling proteins know as Smads. Smad1/5/8 are phosphorylated by the BMP like ligands whereas Smad2/3 are phosphorylated by activins and TGFβs. The term "activin-A" as used herein, refers to the activin isoform βAβA. Activin-A as used for therapeutic purpose in aspects of the present invention is preferably human activin A, such as recombinant human activin-A.

The term "activin receptor" as used herein, refers to any receptor that upon binding of its ligand results in activin signaling as defined herein. The receptor may be, and preferably is, the type-II activin receptor and the ligand may be activin, preferably activin A. However, any given cell may comprise other receptors that trigger activin signaling upon ligand binding. Whether a receptor is an activin receptor as here defined may be tested as follows. If upon receptor activation changes in the expression of the extracellular matrix proteins occur that are analogous (substantially identical) to those observed when activin A binds to the type-II activin receptor as indicated in Tables 1 and 2, then the receptor is defined herein as an activin receptor.

The term "activin inhibitor" is meant to include any compound, and especially any protein (or peptide), which is capable of selectively inhibiting the activity of activin so as to modify any of activin's functions, including suppressing the ability of activin to bind to the activin receptor, in particular activin signalling receptors on the cell surface of the ECM-producing cell. When administered to a subject in need of treatment, the activin-inhibiting compounds of the invention are substantially free of natural contaminants which associate with such compound either in vivo (in a prokaryotic or eukaryotic) host, or in vitro (as a result of a chemical synthesis). Such compounds include, but are not limited to extracellular activin-binding compounds, and intracellular compounds that regulate intracellular activin signalling. Activin-inhibiting compounds within the scope of the methods of the invention also include but are not limited to a) activin-inhibiting compounds that predominantly sequester activin monomers, that is, bind monomers in a complex which is resistant to dimerization; b) activin-inhibiting compounds which sequester activin dimers and prevent activin from interacting with its signaling receptors (for example, follistatin or biologically-active derivatives thereof); or c) prevents activin-signaling by interfering with the activin-signaling cascade in the ECM-producing cell. Follistatin is a soluble protein that functions as an activin binding protein preventing activin from interaction with its signaling receptor.

Anti-Activin A antibodies may be used in embodiments of the present invention as ligand-inhibitors. If desired, such compounds may be administered in the form of a pharmaceutically acceptable salt to the subject.

The term "activin signaling" as used herein refers to the receptor-mediated activation of cellular processes caused by ligand binding to an activin receptor, which activation may be directly or indirectly coupled to the cell's response to the ligand. Indirect coupling refers to the necessity of the activated receptor to interact with other proteins inside the cell before the ultimate physiological effect of the ligand on the cell's behavior is produced. Often, the behavior of a chain of several interacting cell proteins is altered following receptor activation. The entire set of cell changes induced by receptor activation is often referred to as a signal transduction pathway and usually culminates in specific changes at the level of transcription and expression of genes. Activin signaling as used herein thus refers to the signal transduction pathway that can be best defined by the specific changes in expression of the extracellular matrix proteins indicated in Tables 1 and 2 below. Thus, in order to determine whether a substance is an agonist or functional analogue to activin A, the ability of the substance to interact with the activin receptor and the resulting changes in the expression of the extracellular matrix proteins indicated in Tables 1 and 2 below may be evaluated. If the substance interacts with the activin receptor and thereby causes changes in the expression of the extracellular matrix proteins indicated in Tables 1 and 2 analogous (substantially identical) to those effected by activin A, preferably when binding thereof occurs to the activin II receptor, then the substance is an agonist or functional analogue.

The term "mineralization" as used herein, refers to the general process of calcium phosphate deposition on an extracellular matrix. The term is equivalent to the term "calcification". The latter term is also used herein in connection with pathological calcium phosphate depositions on extracellular matrices such as in disease conditions.

The term "ossification" is used to refer to the normal, physiological process of bone formation, in particular associated with osteoblasts.

The term "calcium phosphate" as used herein, refers to in particular to calcium phosphates that are obtained by precipitation from an aqueous solution at low temperature. Highly preferred calcium phosphates are the calcium orthophosphates, which represent a family of compounds that contain a calcium cation, $Ca^{2+}$, and a phosphate anion, $PO_4^{3-}$. There are multiple calcium orthophosphates, including monocalcium orthophosphate (monobasic), dicalcium orthophosphate (dibasic), tricalcium orthophosphate (tribasic), and hydroxyapatite (penta calcium triphosphate), all of which may be deposited on the ECM during its mineralization.

An "effective amount" of a ligand, ligand-inhibitor, inducers, agonist, antagonist or functional analogue is one, which is sufficient to achieve the effect of controlling mineralization of the ECM at the desired location and with the desired magnitude in vivo or in vitro.

The term "therapeutically effective amount" as used herein refers to an amount of a therapeutic agent to treat, ameliorate, or prevent a desired disease or condition, or to exhibit a detectable therapeutic or prophylactic effect. The precise effective amount needed for a subject will depend upon the subject's size and health, the nature and extent of the condition, and the therapeutics or combination of therapeutics selected for administration. Thus, it is not useful to specify a therapeutically effective amount in advance. However, the therapeutically effective amount for a given situation can be determined by routine experimentation.

An "agonist" of a receptor means a compound which binds to the receptor and for which such binding has a similar functional result as binding of the natural, endogenous ligand of the receptor. That is, the compound must, upon interaction with the receptor, produce the same or substantially similar transmembrane and/or intracellular effects as the endogenous ligand. Thus, an agonist of an activin receptor binds to the receptor and such binding has the same or a similar functional result as ligand binding (e.g., inhibition of mineralization). The activity or potency of an agonist can be less than that of the natural ligand, in which case the agonist is said to be a "partial agonist," or it can be equal to or greater than that of the natural ligand, in which case it is said to be a "full agonist" Thus, for example, a small peptide or other molecule which can mimic the activity of a ligand in binding to and activating the ligand's receptor may be employed as an equivalent of the ligand. Preferably the agonist is a full agonist, but partial receptor agonists may also be advantageously employed. Methods of identifying such agonists are readily foreseeable by one of skill in the art and include assays for compounds which induce activin-signaling-mediated responses (e.g., inhibition of matrix maturation, and the like). Such an agent may also be referred to as a ligand "mimic," "mimetic," or "analogue".

The term "analogues" refers to closely related members of a chemotype—a family of molecules that demonstrate a unique core structure or scaffold—wherein the members exhibit minor chemical modifications relative to each other. An "analogue" as referred to herein refers to a compound that exhibits minor chemical modifications, such as chemical substitution of certain chemical groups, relative to an indicated compound, i.e. a chemical derivative. The analogue essentially exhibits comparable biological activity as the indicated compound, i.e. inhibition or stimulation of activin-A signaling, but may provide advantages over the indicated compound such as longer half-life, resistance to degradation, improved target-binding affinity, higher potency, less toxicity or higher tolerability.

A "functional analogue" of an activin-A is a chemical derivative, which possesses a biological activity that is substantially similar to the biological activity of activin-A. By "substantially similar" is meant activity, which is quantitatively different but qualitatively the same. The term "functional analogue" is intended to include the "fragments," "analogues," "derivatives," or "chemical derivatives" of a molecule. Fragments of activin-A herein refer to biologically-active fragments of activin-A which retain the capacity to initiate activin-signaling. An "analogue" of activin-A is meant to refer to a compound substantially similar in function to either native activin-A or to a fragment thereof. For example, an analogue of activin-A is a protein which does not have the same amino acid sequence as activin-A but which is sufficiently homologous to activin-A so as to retain the biological activity of activin-A. For example, a functional derivative of activin-A would contain the same amino acid backbone as activin-A but also contains other modifications such as post-translational modifications such as, for example, bound phospholipids, or covalently linked carbohydrate, depending on the necessity of such modifications for the performance of the therapeutic treatment. As used herein, the term is also meant to include a chemical derivative of activin-A. Such derivatives may improve the compound's solubility, absorption, biological half life, etc. The derivatives may also decrease the toxicity of the molecule, or eliminate or attenuate any undesirable side effect of the molecule, etc. Derivatives and specifically, chemical moieties capable of mediating such effects are disclosed in Remington's Pharmaceutical Sciences (1980). Procedures for coupling such moieties to a molecule are well known in the art.

The term "functional analogue" further covers such compounds that are not chemically related but that for instance block an inhibitor of the primary compound. For instance, follistatin as an inhibitor of activin-A may be inhibited by a follistatin-binding protein thus acting as decoys for follistatin in order to neutralize follistatin and ultimately enabling activation of activin signaling by activin-A.

The term "administration" is meant to include introduction of the therapeutic compounds to a subject in need thereof by any appropriate means known to the medical art, including, but not limited to, enteral and parenteral (e.g., intravenous) administration.

The term "pharmaceutically acceptable salt" is intended to include salts of the therapeutic compounds used in aspects of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

The term "pharmaceutically acceptable vehicle" is intended to include solvents, carriers, diluents, and the like, which are utilized as additives to preparations of the therapeutic compounds used in aspects of the invention so as to provide a carrier or adjuvant for the administration of such compounds.

The "cell" in aspects of the present invention include, but are not limited to, osteoblasts, mesenchymal stem cells, chondrocytes, smooth muscle cell (in particular vascular smooth muscle cells); fibroblasts, mesenchymal cells and adipocytes.

The term "subject" is meant to include all animals, preferably a mammal, most preferably a human in which enhancement of the mineralization of the ECM is desired and wherein said mineralization is beneficial to the physiology of the animal, or wherein prevention of the mineralization of the ECM is desired and wherein said mineralization would be detrimental to the physiology of the animal. Foremost among such animals are humans; however, the invention is not intended to be so limiting, it being within the contemplation of the present invention to treat any and all animals which may experience the beneficial effect of the invention.

Basic Description of the Mechanism for Controlling Mineralization of Extracellular Matrix Transforming growth factor-β (TGFβ) and bone morphogenic protein (BMP) are well known regulators of bone formation. Both TGFβ and BMP promote bone development by stimulating the differentiation of osteoblast progenitor cells. TGFβ is also believed to inhibit later phases of osteoblast differentiation and mineralization. Activins belong to the TGFβ superfamily, however their role in bone formation is relatively unknown and less well studied compared to TGFβs. The structure of activins is closely related to the TGFβs and they act via similar intracellular signaling molecules. Activins and their relatives inhibins were initially purified from gonadal fluids and were characterized based upon their ability to modulate FSH secretion from pituitary gonadotropes (see reviews by Chen et al. Exp Biol Med, 2006. 231: 534-44; Bilezikjian et al. Mol Cell Endocrinol, 2004. 225:29-36).

Besides the classical role of activins as modulators of FSH secretion, activins perform regulatory functions in other cell types and tissues, e.g. the adrenal gland, liver, neurons and pancreas.

Various publications report that activin-A enhances bone formation. For instance, Centrella et al. (Mol Cell Biol, 1991. 11:250-8) show that activin-A acts similar to TGF-β in that it enhances collagen and DNA synthesis in osteoblasts. Ogawa et al. (J Biol Chem, 1992. 267:14233-7) show that activin in combination with bone morphogenetic protein (BMP-2, BMP-3) enhances formation of ectopic bone on a collagen/ceramic carrier implant in vivo. Gaddy-Kurten et al. (Endocrinology, 2002. 143:74-83) demonstrate that activin stimulates osteoblastogenesis, which stimulation is antagonised by inhibin. Sakai et al. (Bone, 1999. 25(2):191-6) show that activin promotes callus formation, increases mechanical strength of bone and promotes endochondral bone formation during bone fracture healing. Sakai et al. (Bone, 2000. 27:91-6) and Sakai & Eto (Mol Cell Endocrinol, 2001. 180:183-8) demonstrate that systemic administration of activin in aged ovariectomized rats increases bone mass and mechanical strength of vertebrae, and suggest that activin may be used in the therapy of fracture and osteoporosis. Hirotani et al. (Calcif Tissue Int, 2002. 70:330-8) show that the topical administration of activin A in isografted bone of mice stimulates periosteal bone formation and increases bone mass.

In summary, many reports indicate that activin promotes osteogenesis in murine bone marrow cultures and promotes bone formation and fracture healing in vivo in rodents.

The present inventors have discovered that activin-signaling in osteoblasts and VSMCs affects maturation of the ECM excreted by these cells, thereby keeping the ECM in an immature state and effectively preventing it from being mineralized. Thus, activin-signaling at an early moment in the development of the ECM is most effective in preventing its mineralization.

As a result of these findings, the present inventors have discovered that mineralization of, or calcium phosphate deposition on, an extracellular matrix, in particular the mature extracellular matrix of osteoblasts or VSMCs, can be prevented or suppressed by activin-A. In contrast, mineralization of an extracellular matrix, in particular a mature ECM of osteoblasts or VSMCs, can be promoted or stimulated by activin-A inhibitors, such as follistatin.

Both these findings now enable the provision of methods for controlling ECM mineralization in both directions. The ability to control mineralization in both directions is thus based on the finding that ECM maturation is essential to subsequent mineralization, and that this maturation is controlled activin-A.

The present inventors have thus discovered that activin-A plays an important role in ECM production and maturation that leads to mineralization and that activin-A exerts an inhibitory effect on mineralization via structuring of the immature ECM and thus of the osteoid. In summary, the inventors have discovered that:

1) human osteoblasts express activin A and its natural inhibitor follistatin to control activin signaling in a differentiation-dependent manner, 2) activin inhibits mineralization in a human bone formation model as well as in a model for vascular mineralization, and 3) activin does so by changing the expression of a wide range of matrix proteins prior to the onset of mineralization leading to a matrix composition with no or reduced mineralizing capacity.

This led to the conclusions that activin signaling is a potent regulator of bone matrix formation and mineralization and thereby an interesting mechanism in the control and maintenance of bone quality. Using activin A, follistatin, or analogues of these compounds, mineralization can be controlled in two directions. As a consequence, activin signaling and activin target genes are important therapeutic targets to control matrix mineralization in bone as well as mineralization in pathological conditions.

A schematic presentation of the control mechanism may be provided as follows:

| | Activin A* | Activin A inhibitor | Follistatin* | Follistatin inhibitor |
|---|---|---|---|---|
| Mineralization | Inhibited | Stimulated | Stimulated | Inhibited |

*or analogs thereof

The above described basic mechanism has provided the insight that the biological basis of this control mechanism resides in interference with normal receptor-ligand interaction, and thus that the mineralization process, be it pathological or normal, is at least partly controlled at the level of the receptor-ligand interaction associated with the activin receptor, and thus at the level of activin signaling. Once this was realized, scientific proof for this hypothesis was found in the ability to manipulate the expression of genes encoding specific extracellular matrix proteins by interfering in the interaction between activin receptor and ligand. In particular it was found that the expression of certain genes that encode a protein or glycoprotein which is part of the ECM, is enhanced as a result of an activin challenge, while the expression of other genes is enhanced as a result of a follistatin challenge (See FIG. 8).

Since activin was found to be involved in inhibition of matrix maturation and/or mineralization, it should be concluded that genes that show enhanced expression upon activin challenge, and that are consequently the cellular response initiated by activin (i.e. the activin target genes), are also associated with inhibition of matrix maturation and/or mineralization.

The genes encoding a protein or glycoprotein which is part of the ECM that are up-regulated (expression is increased) as a result of activin exposure are the genes for periostin, osteoblast specific factor (POSTN); matrix metallopeptidase 2 (MMP2); biglycan (BGN); Sparc/osteonectin, cwcv and kazal-like domains proteoglycan (testican) (SPOCK1); fibulin 5 (FBLN5); latent transforming growth factor beta binding protein 2 (LTBP2); chondroitin sulfate proteoglycan 2 (versican) (VCAN); hyaluronan and proteoglycan link protein 1 (HAPLN1); collagen type VIII alpha 2 (COL8A2); collagen type XVI alpha 1 (COL16A1); collagen triple helix repeat containing 1 (CTHRC1); ADAM metallopeptidase with thrombospondin type 1 motif (ADAMTS3); collagen type V alpha 1 (COL5A1); and thrombospondin 1 (THBS1). Thus, up-regulation or enhancement of the expression of these genes will result in inhibition or prevention of matrix maturation and/or mineralization. Conversely, down-regulation of such genes stimulates or enhances maturation and/or mineralization.

The genes encoding a protein or glycoprotein which is part of the ECM that are down-regulated (expression is decreased) as a result of activin A exposure are the genes for C-type lectin domain family 3, member B (CLEC3B); Collagen type V, alpha 3 (COL5A3); Nidogen 2 (osteonidogen) (NID2); TIMP metallopepetidase inhibitor 4 (TIMP4); Papilin, proteoglycon-like sulfated glycoprotein (PAPLN); Collagen, type IV, alpha 6 (COL4A6); Dystrobrevin, alpha (DTNA); CD248 antigen, endosialin (CD248); Matrilin 2 (MATN2); and Elastin microfibril interfacer 2 (EMILIN2). Thus, up-regulation or enhancement of the expression of these genes will result in stimulation or enhancement of matrix maturation and/or mineralization. Conversely, upregulation of such genes inhibits or prevents matrix maturation and/or mineralization.

Since follistatin was found to be involved in stimulation of matrix maturation and/or mineralization, it should be concluded that genes encoding a protein or glycoprotein which is part of the ECM that show enhanced expression upon follistatin challenge are also associated with stimulation of matrix maturation and/or mineralization. The genes that are upregulated (expression is increased) as a result of follistatin exposure are the genes for CD248 antigen, endosialin; Elastin microfibril interfacer 2; Matrilin 2; Dystrobrevin, alpha; Collagen, type IV, alpha 6; Nidogen 2 (osteonidogen); Papilin, proteoglycan-like sulfated glycoprotein; C-type lectin domain family 3, member B; Collagen type V, alpha 3; TIMP metallopepetidase inhibitor 4. Thus, upregulation or enhancement of the expression of these genes will result in stimulation of matrix maturation and/or mineralization. Conversely, downregulation of such genes inhibits or prevents maturation and/or mineralization.

TABLE 1

Extracellular matrix proteins up-regulated by activin A (downregulated by follistatin).

| Gene Symbol | Gene description | Affymetrix ID | day 5 FST | day 5 Act. A | day 12 FST | day 12 Act. A |
|---|---|---|---|---|---|---|
| POSTN | Periostin, osteoblast specific factor | 210809_s_at | −1.46 | 2.26 | −0.73 | 1.56 |
| MMP2 | Matrix metallopeptidase 2 | 201069_at | −0.68 | 1.92 | −0.91 | 1.28 |
| BGN | Biglycan | 201261_x_at; 201262_s_at; 213905_x_at | −0.57 | 1.68 | −0.67 | 0.97 |
| SPOCK1 | Sparc/osteonectin, cwcv and kazal-like domains proteoglycan (testican) | 202363_at | −0.31 | 1.57 | −0.36 | 1.84 |
| FBLN5 | Fibulin 5 | 203088_at | −0.09 | 1.44 | −0.64 | 2.60 |
| LTBP2 | Latent transforming growth factor beta binding protein 2 | 204682_at | −0.64 | 1.35 | −0.65 | 0.73 |
| VCAN | Chondroitin sulfate proteoglycan 2 (versican) | 204620_s_at; 204619_s_at; 211571_s_at; 221731_x_at | −0.99 | 1.26 | −0.33 | 0.77 |
| HAPLN1 | Hyaluronan and proteoglycan link protein 1 | 205523_at; 205524_s_at | −0.68 | 1.09 | −0.34 | 0.92 |
| COL8A2 | Collagen, type VIII, alpha 2 | 52651_at; 221900_at | −0.58 | 1.01 | −0.20 | 0.72 |
| COL16A1 | Collagen, type XVI, alpha 1 | 204345_at | −0.26 | 0.91 | −0.60 | 0.71 |
| CTHRC1 | Collagen triple helix repeat containing 1 | 225681_at | −0.68 | 0.85 | −0.18 | 0.96 |
| ADAMTS3 | ADAM metallopeptidase with thrombospondin type 1 motif, 3 | 214913_at | −0.42 | 0.62 | −0.28 | 0.33 |
| COL5A1 | Collagen, type V, alpha 1 | 203325_s_at; 212488_at; 212489_at | −0.43 | 0.62 | −0.38 | 0.68 |
| THBS1 | Thrombospondin 1 | 201107_s_at | −0.36 | 0.15 | −0.85 | 0.64 |

Extracellular matrix proteins were identified on basis of the selection criteria shown in FIG. 7A. The Genes are sorted on basis of the effect of Activin A on day 5. The log2 fold changes shown are with respect to vehicle treatment at the same day. Vehicle values are not shown. FST = follistatin; Act. A = Activin A.

TABLE 2

Extracellular matrix proteins down-regulated by activin A (up-regulated by follistatin).

| Gene Symbol | Gene description | Affymetrix ID | day 5 FST | day 5 Act. A | day 12 FST | day 12 Act. A |
|---|---|---|---|---|---|---|
| CLEC3B | C-type lectin domain family 3, member B | 205200_at | 1.16 | −1.60 | 1.03 | −1.90 |
| COL5A3 | Collagen, type V, alpha 3 | 52255_s_at; 218975_at | 0.47 | −1.50 | 0.68 | −1.87 |
| NID2 | Nidogen 2 (osteonidogen) | 204114_at | 0.09 | −1.33 | 0.90 | −0.88 |
| TIMP4 | TIMP metallopeptidase inhibitor 4 | 206243_at | 0.68 | −1.31 | 0.51 | −1.26 |

TABLE 2-continued

Extracellular matrix proteins down-regulated by activin A (up-regulated by follistatin).

| Gene | | | day 5 | | day 12 | |
|---|---|---|---|---|---|---|
| Symbol | Gene description | Affymetrix ID | FST | Act. A | FST | Act. A |
| PAPLN | Papilin, proteoglycan-like sulfated glycoprotein | 226435_at | 0.05 | −1.18 | 0.51 | −0.97 |
| COL4A6 | Collagen, type IV, alpha 6 | 213992_at | 0.01 | −0.85 | 0.97 | −0.54 |
| DTNA | Dystrobrevin, alpha | 205741_s_at | 0.09 | −0.82 | 0.49 | −0.63 |
| CD248 | CD248 antigen, endosialin | 219025_at | 0.97 | −0.71 | 0.48 | −0.93 |
| MATN2 | Matrilin 2 | 202350_s_at | 0.03 | −0.46 | 0.50 | −0.88 |
| EMILIN2 | Elastin microfibril interfacer 2 | 224374_s_at | 0.59 | −0.45 | 0.43 | −0.32 |

Extracellular matrix proteins were identified on basis of the selection criteria shown in FIG. 7A. The Genes are sorted on basis of the effect of Activin A on day 5. The log2 fold changes shown are with respect to vehicle treatment at the same day. Vehicle values are not shown.
FST = follistatin;
Act. A = Activin A.

Methods of Controlling Mineralization

Based on the above, the present invention provides a number of methods for improving or preventing mineralization, all of which are based on the insight of selective gene expression as a result of activation of an activin receptor. Thus, the mineralization may be controlled in two directions.

A. Inhibition of ECM Mineralization and Calcification Through Receptor interaction.

In a first direction of controlling mineralization, the mineralization and/or calcification of an ECM is inhibited or prevented. According to a method of the present invention, this inhibition or prevention of mineralization and/or calcification is accomplished by activation of an activin receptor.

Thus, in one aspect, the present invention provides a method for inhibiting or preventing mineralization of an extracellular matrix, comprising the step of activating an activin receptor. It will thus be understood that the present invention can be practiced with methods and compositions comprising e.g. ligands or agonists of an activin receptor, preferably a ligand or agonist of the type II activin receptor.

The term "ligand" as used herein, unless expressly indicated otherwise, is to be understood as referring to an activin receptor ligand. It will be understood that the ligand may be an endogenous ligand, or an exogenous receptor ligand capable of interacting with the activin receptor, i.e. to engage in such interaction that results in activin signaling as defined herein.

In the case that the activin-signaling receptor ligand is the type-II activin receptor, an example of a suitable ligand is activin A.

Alternatively, a ligand stimulating agent or ligand inducer in lieu of a ligand may be used. A "ligand inducer" is a compound that stimulates in vivo production, e.g., expression, of a therapeutically effective concentration of an endogenous receptor ligand in the body of a mammal sufficient to achieve activation of the receptor, which in the case of activin A refers to a concentration sufficient to maintain or stimulate ECM mineralization or to inhibit ECM mineralization as required. Such compounds are understood to include substances which, when administered to a mammal, act on cells of tissue(s) or organ(s) that normally are competent to produce and/or secrete a ligand encoded within the genome of the mammal, and which cause the endogenous level of the ligand in the mammal's body to be altered. Endogenous or administered ligands can act as endocrine, paracrine or autocrine factors. That is, endogenous ligands can be synthesized by the cells that produce the ECM, by neighbouring cells, or by cells of a distant tissue, in which circumstances the secreted endogenous ligand is transported to the site of prevention or stimulation of mineralization, e.g., by the individual's bloodstream. In preferred embodiments, the agent stimulates expression and/or secretion of an endogenous ligand so as to increase amounts thereof in the tissue in which ECM mineralization is to be controlled.

In still other embodiments, an agent which acts as an agonist of an activin receptor may be administered instead of the ligand itself.

In still further embodiments, functional analogues of the ligand may be used. A suitable functional analogue is for instance a follistatin-binding protein or an antibody against follistatin. Such compounds are effective inhibitors of ligand-inhibitors, thereby preventing the ligand inactivation and allowing the activation of the receptor.

The ligands, inducers, agonists and functional analogues of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and intracapsular. In other applications, such as where surgical implants are the subject of calcification, the implant itself may be impregnated with the ligand, inducer or agonist. Very suitable, the implant material may form or comprise a slow-release matrix, capable of releasing the compound over a period of time at a predetermined location. Treatments are also preferably conducted over an extended period, preferably on an outpatient basis with daily dosages for active compounds in the range of about 0.01-1000 µg/kg body weight, and more preferably about 0.1-100 µg/kg body weight.

A method of the present invention for inhibiting or preventing mineralization of an extracellular matrix may be used in various therapeutic and non-therapeutic applications. For instance, therapeutic application of a method for inhibiting or preventing mineralization of an extracellular matrix may be found in treating or preventing pathological calcification. Examples of such pathological calcification processes are listed in Table 3, below.

TABLE 3

Conditions of pathological mineralization

| Tissue | Disease | Clinical pattern |
|---|---|---|
| Blood vessels | Atherosclerosis | Calcification bone formation in/around vascular smooth muscle cells |
| Heart | Heart valve calcification | Calcification in/around myotibroblasts |

TABLE 3-continued

Conditions of pathological mineralization

| Tissue | Disease | Clinical pattern |
|---|---|---|
| Joints | Tendonitis | Calcification of the tendon |
|  | Arthritis | Calcification of articular cartilage |
|  | Bursitis | Calcification of bursal walls |
|  | Bone spurs | Osteophytes in osteoarthritis |
| Skin | Cutaneous ossification | Bone formation in the skin |
| Kidney | Kidney stones | Calcium oxalate or calcium Pi stones |
| Muscles | Myositis ossificans | Bone formation in the muscles |
| Lung | Metastatic pulmonary | Calcification in alveolar septa |
|  | Pulmonary ossification | Bone formation in alveolar compartments |
| Eyes | Cataracts | Calcification of the lens |
| Brain | Bilateral Striopallidodentate calcinosis | Symmetric calcification of the basal ganglia |
| Spinal cord | Neurogenic heterotopic ossification | Bone formation in spinal cord |
| Tumor | Osteosarcoma | Bone cancer that may metastasize elsewhere |

Thus, in a preferred embodiment of a method for inhibiting or preventing mineralization of an extracellular matrix, the mineralization is a pathological calcification. Such calcifications may occur in various tissues, either in direct association with those tissues as a result of a pathological condition, or associated with synthetic, semi-synthetic or tissue engineered implants in such tissues; all of such calcifications are collectively addressed as pathological. Preferably said pathological calcification is selected from the group consisting of atherosclerotic calcification, metastatic pulmonary calcification, heart valve calcification, and the calcifications associated with tendonitis; arthritis; bursitis; bone spurs; cutaneous ossification; kidney stones; myositis ossificans; pulmonary ossification; cataracts; bilateral striopallidodentate calcinosis; neurogenic heterotopic ossification and osteosarcoma.

Also, various non-therapeutic applications of methods of the present invention are provided. For instance the calcification of cartilage in in vitro or ex vivo tissue engineering applications, in particular in tissue culture of chondrocytes.

B. Stimulation of ECM Mineralization and Calcification Through Receptor Interaction.

In a second direction of controlling mineralization, the mineralization and/or calcification of an ECM is stimulated. The stimulation of mineralization is accomplished by prevention of the interaction between a activin receptor and its endogenous ligand.

Therefore, in another aspect, the present invention provides a method for stimulating mineralization of an extracellular matrix, comprising the step of preventing the interaction between an activin receptor and its endogenous ligand. It will thus be understood that the present invention can be practiced with methods and compositions comprising a scavenger or inhibitor of a ligand of an activin receptor, an inducer of said ligand-inhibitor or an antagonist of said receptor. The skilled person will understand that the embodiments of this aspect of the invention, relating to the stimulation of mineralization, are analogous but opposite to those described above for inhibition of mineralization. It will thus be understood that the present invention can be practiced with methods and compositions comprising an inhibitor of a ligand of an activin receptor.

The term "inhibitor of a ligand" or its equivalent "ligand-inhibitor" as used herein, unless expressly indicated otherwise, is to be understood as referring to an activin receptor ligand-inhibitor. It will be understood that the ligand-inhibitor may be an endogenous inhibitor, or an exogenous inhibitor.

In the case that the activin receptor ligand is the type-II activin receptor and the ligand is activin A, a suitable ligand-inhibitor is follistatin, Alternatively, and similar as described above, a ligand-inhibitor stimulating agent or ligand inducer in lieu of a ligand may be used.

In still other embodiments, an agent that acts as an antagonist to the receptor that is to be activated may be administered to block the receptor. An "antagonist" of a receptor means a compound which, when it binds to a receptor, blocks the receptor but doesn't stimulate it and prevents a signaling response from occurring or lowers the intensity of the response.

The ligand-inhibitors, inducers of ligand inhibitors and antagonists of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and intracapsular. In other applications, such as where rapid ossification of surgical implants is required, the implant itself may be impregnated with the ligand-inhibitor, ligand-inhibitor inducer or antagonist. Very suitable, the implant material may form or comprise a slow-release matrix, capable of releasing the compound over a period of time at a predetermined location. Treatments are also preferably conducted over an extended period, preferably on an outpatient basis with daily dosages for active compounds in the range of about 0.01-1000 µg/kg body weight, and more preferably about 0.1-100 µg/kg body weight.

A method of the present invention for stimulating mineralization of an extracellular matrix may be used in various therapeutic and non-therapeutic applications. For instance, therapeutic application of a method for stimulating mineralization of an extracellular matrix may be found in treating or preventing osteoporosis and in bone healing. Non-therapeutic applications include synthetic bone production in cell cultures and ossification in tissue engineering.

C. Inhibition of ECM Mineralization and Calcification Through Alteration of Gene Expression.

As noted above, several genes have been identified that are targeted by activin signalling and that are up-regulated as a result of such signaling, As an elaboration of this, the present invention provides a method for inhibiting or preventing matrix maturation and/or mineralization by enhancing the expression of at least one gene selected from the group consisting of thrombospondin 1; collagen type V alpha 1; collagen type XVI alpha 1; collagen type VIII alpha 2; collagen triple helix repeat containing 1; hyaluronan and proteoglycan link protein 1; chondroitin sulfate proteoglycan 2 (versican); latent transforming growth factor beta binding protein 2; biglycan; matrix metallopeptidase 2; periostin, osteoblast specific factor; fibulin 5; SPOCK1, Sparc/osteonectin, cwcv and kazal-like domains proteoglycan (testican); and ADAM metallopeptidase with thrombospondin type 1 motif.

Up-regulation or enhancement of gene expression can for instance be accomplished by gene therapy. Alternatively, as noted above, several genes of extracellular matrix proteins have been identified whose expression is also affected by activin signalling but in an opposite manner, i.e., whose expression is up-regulated as a result of follistatin exposure, As an elaboration of this, the present invention provides a method for inhibiting or preventing matrix maturation and/or mineralization by blocking the expression of at least one gene selected from the group consisting of the genes for CD248 antigen, endosialin; elastin microfibril interfacer 2; matrilin 2; dystrobrevin, alpha; collagen, type IV, alpha 6; nidogen 2 (osteonidogen); papilin, proteoglycon-like sulfated glycoprotein; C-type lectin domain family 3, member B; collagen type V, alpha 3; and TIMP metallopepetidase inhibitor 4.

Blocking of gene expression may for instance be accomplished by such methods as RNAi, which are well known to those of skill in the art.

D. Stimulation of ECM Mineralization and Calcification Through Alteration of Gene Expression.

Contrary to the methods described above for inhibition of ECM mineralization, the present invention provides a method for stimulating matrix maturation and/or mineralization by i) blocking the expression of at least one gene selected from the group consisting of thrombospondin 1; collagen type V alpha 1; collagen type XVI alpha 1; collagen type VIII alpha 2; collagen triple helix repeat containing 1; hyaluronan and proteoglycan link protein 1; chondroitin sulfate proteoglycan 2 (versican); latent transforming growth factor beta binding protein 2; biglycan; matrix metallopeptidase 2; periostin, osteoblast specific factor; fibulin 5; SPOCK1, Sparc/osteonectin, cwcv and kazal-like domains proteoglycan (testican); and ADAM metallopeptidase with thrombospondin type 1 motif; or ii) enhancing the expression of at least one gene selected from the group consisting of the genes for CD248 antigen, endosialin; elastin microfibril interfacer 2; matrilin 2; dystrobrevin, alpha; collagen, type IV, alpha 6; nidogen 2 (osteonidogen); papilin, proteoglycon-like sulfated glycoprotein; C-type lectin domain family 3, member B; collagen type V, alpha 3; and TIMP metallopepetidase inhibitor 4.

DESCRIPTION OF PARTICULARLY PREFERRED EMBODIMENTS

A method for selecting a candidate therapeutic agent for controlling mineralization of an extracellular matrix in a tissue of a subject comprising the step of exposing a cell from said tissue that produces an extracellular matrix to a test compound under conditions that support extracellular matrix formation and matrix maturation.

The term "conditions that support extracellular matrix formation and matrix maturation" refers to culture conditions for cultivated cells wherein the cells are provided with the nutrients, growth factors and other supplements necessary for the ECM to be formed around the cells and to potentially reach a composition that can be mineralized (for instance by living osteoblasts), which composition is referred to as "mature". In particular the term "conditions that support extracellular matrix formation and matrix maturation" refers to such conditions during a period running from the onset of formation of the extracellular matrix and the onset of mineralization of the extracellular matrix, preferably not including the mineralization and therefore preferably not including mineralizing conditions. Generally the cultivation period for SV-HFO and NHOst cells between the onset of the formation of an extracellular matrix and the onset of mineralization is between day 5 and day 12, but may change from cell-type to cell-type. Thus, the term "conditions that support extracellular matrix formation and matrix maturation" refers to in particular to conditions during the pre-mineralization period.

The term "mineralizing conditions" refers to the culture conditions for cultivated cells wherein the cells are provided with the nutrients, growth factors and other supplements necessary for the ECM to mineralize. In particular such conditions require the presence of mineralizable source of calcium and often beta-glycerophosphate.

The culture of an extracellular matrix-producing cell under conditions that produce a mineralized matrix (i.e. the "mineralizing condition") is well known in the art and may differ between cell types.

Extracellular matrix producing cells, preferably human osteoblasts, human mesenchymal stem cells or human vascular smooth muscle cells can be cultured in a general cell culture medium such as minimum Essential Medium Alpha (αMEM) or Dulbecco's Modification of Eagle's Medium (DMEM), preferably supplemented with serum (preferably Bovine Calf Serum). In essence such media are able to support extracellular matrix formation and maturation. In order to provide for mineralizing conditions a suitable calcium-phosphate source must be provided. Very suitably, in order to provide for mineralizing conditions, cell cultures are cultured without subculturing for a period up to 30 days in the presence of steroid hormones (in particular glucocorticoids, preferably dexamethasone or cortisol), optionally in the presence of ascorbic acid, and with a suitable calcium source such as calcium chloride and a suitable phosphate source such as β-glycerophosphate (both required for deposition in the form of a calcium phosphate). Cultivation may occur under normal cell culture conditions (at 37° C. and 5% $CO_2$ in a humidified atmosphere).

Conditions that support extracellular matrix formation and matrix maturation can be provided by cells with the same culture conditions as for mineralizing conditions with the exception that the glucocorticoids and/or calcium and/or phosphate sources are omitted, small amounts of calcium and phosphorous are required for normal cell function, but amounts required for mineralization can optionally be omitted. Very suitable conditions are for instance provided by cultivation in an appropriate cell culture medium such as αMEM or DMEM supplemented with serum as described above, preferably without subculturing for a period of up to 30 days under normal cell culture conditions.

In order to expose the cells to the test compound under conditions that support extracellular matrix formation and matrix maturation the test compound is suitably added to the culture medium. The concentration of the test compound in which it is provided to the cell during the subject exposure is not particularly limiting. Very suitably, the concentration of the test compound is about 1 to about 1000 ng/ml.

As test compounds one may choose small chemical molecules, nucleic acids, proteins, peptides, carbohydrates, lipids, and combinations thereof.

A method for selecting a candidate therapeutic agent for controlling mineralization of an extracellular matrix in a tissue of a subject (which may include a natural tissue or an artificial tissue as used in tissue engineering) further comprising the step of determining the expression in said cell of at least one gene in response to said exposure. This determination is preferably performed during the pre-mineralization period, that is generally between 5 and 12 days after the cells have been provided with conditions that support extracellular matrix formation and matrix maturation. Determining the expression level of a gene in a cell is routine practice for the skilled person. The expression level can be determined by micro-array analysis as described in the Examples below. Generally, micro-array expression profiling is routine practice, and involves the measurement of cDNA prepared from mRNA isolated from cells of interest on a DNA chip array. Alternatively, the level can be determined, by measuring the level of individual mRNAs by quantitative RT-PCR (qPCR) or equivalent methods. In a further alternative embodiment, the level of expression can be determined at the level of the protein. Such methods may for instance be performed by using mass-spectrometric methods for proteome analysis or antibody-based methods.

In a method of the invention, the level of expression of only a very limited number of genes needs to be determined in order to assess the potential of a particular test compound to affect the mineralization process. In principle, the detection of one gene of group A and/or B as described herein is sufficient. Preferably, however, the expression level of more than one gene is determined. Preferred numbers of genes of which the expression level of determined are 3, 4, 5, 6, 7, 8, 9, or 10 or even more genes. Most preferably the expression level of 20, 21, 22 or 23 genes is determined.

The genes of which the expression levels are determined are selected from the genes that encode for thrombospondin 1; collagen type V alpha 1; collagen type XVI alpha 1; collagen type VIII alpha 2; collagen triple helix repeat containing 1; hyaluronan and proteoglycan link protein 1; chondroitin sulfate proteoglycan 2 (versican); latent transforming growth factor beta binding protein 2; biglycan; matrix metallopeptidase 2; periostin, osteoblast specific factor; fibulin 5; SPOCK1, Sparc/osteonectin, cwcv and kazal-like domains proteoglycan (testican); and ADAM metallopeptidase with thrombospondin type 1 motif (together hereinafter referred to as group A), and CD248 antigen, endosialin; elastin microfibril interfacer 2; matrilin 2; dystrobrevin, alpha; collagen, type IV, alpha 6; nidogen 2 (osteonidogen); papilin, proteoglycon-like sulfated glycoprotein; C-type lectin domain family 3, member B; collagen type V, alpha 3; and TIMP metallopetidase inhibitor 4 (together hereinafter referred to as group A).

A method for selecting a candidate therapeutic agent for controlling mineralization of an extracellular matrix further comprising the step of determining whether the expression of said at least one gene in said cell is regulated as a direct result of said exposure.

The term "regulated" as used herein, refers to fact that the expression of the gene changes as a direct or indirect consequence of the exposure of the cell to the test compound. The skilled person will understand that a reference measurement is required in order to determine whether the test compound induces the change in the level of expression of the gene in a direct or indirect manner. The skilled person will be able to device the proper assay conditions with which a reference measurement can be obtained. As a guide, one may take as a reference measurement an assay using the vehicle of the test compound. The term "vehicle" as used herein refers to a suitable control substance, such as the carrier, solvent or dilutent of the test compound (i.e. the blanc).

When the expression is regulated as a result of the exposure, the test compound is positively identified as a candidate therapeutic agent for controlling mineralization of an extracellular matrix in a tissue of a subject under study.

Activin-A molecules that are the subject of preferred aspects of the invention may be purified native and recombinant activin-A, and functional analogues thereof, which are characterized by the presence of unique receptor binding domains and which possess the biological activity of initiating activin-signaling in cells having the activin receptors.

The particular activin-A inhibitor molecules that are the subject of aspects of the invention may be purified native and recombinant activin-A inhibitor proteins, and other proteinaceous or non-proteinaceous activin-A inhibitor molecules, and biologically-active fragments thereof, which are characterized by the presence of a unique activin-binding domain which possess the biological activity of being able to sequester activin-A in a monomeric or dimeric form or cause homodimer unbinding or cover receptor-binding sites on free activin-A or by binding to the activin signaling receptor to block binding of activin A. Individual activin-binding domains possessing this biological activity may also be produced by synthetic, enzymatic, proteolytic, chemical or recombinant DNA methods.

In preferred embodiments of aspects of the present invention, follistatin, or activin-binding fragments thereof are used, and for instance provided to the subject in need of treatment in accordance with a therapeutic method of the invention.

In one embodiment, efficacious levels of activin-inhibiting compounds are administered so as to provide the therapeutic benefits of improving the ECM's ability to mineralize.

In the methods of the invention, infusion of activin-inhibiting compounds, such as, for example, follistatin, or activin-inhibiting fragments thereof results initially in a) binding to activin monomers so as to prevent their dimerization into activin-A, and/or b) unbinding of activin-A dimers so as to result in formation of inactive activin-A monomers, and/or c) enhanced clearance of such activin-A dimers complexed to activin-inhibiting compounds from the circulation or extracellular tissue environment and/or d) binding to activin-A dimers so that the biological function of activin-A is blocked. As a result of this inhibition of activin-A, activin-signaling in the cells of the target tissue will be prevented, which leads to enhanced mineralization of the ECM surrounding the target cells.

In the methods of the invention, infusion of activin-A or functional analogues thereof results in activin-signaling in the cells of the target tissue, thereby preventing the ECM surrounding these cells to develop to a maturation stage and effectively maintaining the ECM in a pre-mature stage, which prevents its mineralization.

Thus, depending on the required therapy, a therapeutic compound in aspects of the present invention may be either activin-A inhibitor or activin-A. The therapeutic compounds may be conjugated, either chemically or by genetic engineering, to fragments of other agents which provide a targeting of such compounds to a desired site of action.

Amounts and regimens for the administration of therapeutic compounds can be determined readily by those with ordinary skill in the clinical art of treating mineralization-related disorders, bone formation defects and/or atherosclerosis. Generally, the dosage of treatment will vary depending upon considerations such as: type of compound employed; age; health; conditions being treated; kind of concurrent treatment, if any, frequency of treatment and the nature of the effect desired; extent of tissue damage; gender; duration of the symptoms; and, counter indications, if any, and other variables to be adjusted by the individual physician. Dosage can be administered in one or more applications to obtain the desired results.

The dosage administered should preferably be chosen such that local concentrations are between 2 and 100 ng/ml for activin-A and between about 50 and 500 ng/ml for follistatin. Administration is of course dependent on the kind of compound and the efficacy of the compound. Compounds that are targeted will also generally require administration in lower dosage forms.

The dosage of follistatin as an activin-A inhibitor may suitably be from about 1 to about 1000 ng/ml.

The therapeutic compounds used in aspects of the invention can be administered in any appropriate pharmacological carrier for administration. They can be administered in any form effective in prophylactic, palliative, preventative or curing conditions of mineralization defects in humans and animals.

Preparations of the therapeutic compounds for parenteral administration includes sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The therapeutic compounds may also be administered by means of pumps, or in sustained-release form, especially, when the mineralization defect is prolonged or delayed rather an acute. An example in which the mineralization defect is often prolonged or delayed rather than acute is a defect resulting from osteoporosis, or a defect resulting from atherosclerosis wherein the calcification of the sclerotic plaque is absent or incomplete. The therapeutic compounds may also be delivered to specific organs in high concentration by means of suitably inserted catheters, or by providing such molecules as a part of a chimeric molecule (or complex) which is designed to target specific organs.

Administration in a sustained-release form is more convenient for the subject when repeated injections for prolonged periods of time are indicated. For example, it is desirable to administer the therapeutic compounds in a sustained-release form when the methods of the invention are being used to treat a genetic or chronic disease based upon a mineralization-related disorder so as to maximize the comfort of the subject.

The therapeutic compounds can be employed in dosage forms such as tablets, capsules, powder packets, liquid solutions for parenteral injection into the body, or liquid solutions for enteral (oral) administration if the biological activity of the therapeutic compound is not destroyed by the digestive process and if the characteristics of the compound allow it to be absorbed across the intestinal tissue.

Pharmaceutical compositions for use in aspects of the present invention can be obtained by mixing the medicament with a pharmaceutically acceptable carrier.

The pharmaceutical compositions for use in aspects of the present invention are manufactured in a manner which is in itself know, for example, by means of conventional mixing, granulating, dragee-making, dissolving, lyophilizing or similar processes. The compositions find utility in the control of mineralization-related disorders, be it chronic or acute. The compositions direct the body's own mechanisms associated with mineralization of extracellular matrix materials. In high potency versions, the compositions used in aspects of the invention have a sufficiently rapid onset of action to be useful in the acute management of ECM mineralization.

Additionally, a low potency version is useful in the management of mild or chronic mineralization-related disorders.

Activin-A and activin-A inhibiting proteins or other activin-A inhibiting compounds which are substantially free of natural contaminants can be isolated and purified from their natural or recombinant sources in accordance with conventional conditions and techniques in the art previously used to isolate such proteins and/or compounds, such as extraction, precipitation, chromatography, affinity chromatography, electrophoresis, or the like.

One of skill in the art can identify the activin-binding domain(s) of an activin-inhibiting compound using techniques known in the art, without undue experimentation, and such domains are preferred in the methods of the invention. For example, derivatives of the native activin-inhibiting proteins, or, derivatives of recombinantly produced activin-inhibiting proteins, can be made by proteolytic cleavage of the full-length activin-inhibiting protein with common proteases, such as, for example, trypsin, chymotrypsin, and subtilisin. Affinity chromatography with activin-derivatized resins may be used to assay such fragments for their activin-binding ability.

Further, compounds such as activin-A and follistatin are highly conserved among species and can be easily isolated in large quantities from nonhuman sources and fragments of these proteins can be chemically or enzymatically prepared by techniques well-known in the art. Thus such compounds can be administered to a subject in need of the therapeutic methods of the invention without provoking a severe immune response.

In one embodiment, a method of the present invention may be performed by exposing the cell that produces the ECM to an effective amount of activin-A or a functional analogue thereof.

In another embodiment, a method of the present invention may be performed by blocking said type-II activin receptor. A suitable type-II activin receptor blocker is Cripto (as described in Harrison et al., Trends in endocrinology and metabolism, 2005, 16:73-78. Alternatively, one may provide cells with a truncated or a dominant negative form of activin type II or type I receptor, which is known to block activin signaling.

In still another embodiment, a method of the present invention may be performed by inhibiting activin-A. A very suitable activin inhibitor is follistatin. Yet, other inhibitors may also be used. Suitable examples are activin-A antibodies, which effectively block the receptor-binding part of the protein.

The present invention now provides a method wherein during the formation of the extracellular matrix, the cells are exposed to activin-A or an activin-A inhibitor.

It is to be understood that the extracellular matrix, produced by the ECM-producing cells upon treatment according to a method of the present invention, is itself part of the present invention. Such an extracellular matrix material may find utility in applications where a material is required that does not mineralize when exposed to a mineralizing environment. Alternatively, such an extracellular matrix material may find utility in applications where a material is required that rapidly mineralizes when exposed to a mineralizing environment. Modulation of specific ECM proteins identified as being regulated by activin signaling may thus also be used to control mineralization of the ECM. A used herein, a mineralizing environment is usually to be understood as a cellular environment, for instance an environment comprising calcium-phosphate depositing osteoblasts, although the presence of cells is not essential, as long as the biochemical factors necessary for calcium phosphate formation and deposition, such as osteocalcin, osteonectin, osteoprotegerin, and/or bone sialoprotein (which can act as a nucleator of calcium phosphate formation) and a source of calcium phosphate are provided to said matrix to such an extent that mineralization can occur.

A very suitable application of a method of the invention is the provision of tissue regeneration scaffolds that rapidly mineralize, and wherein said mineralization may occur either in vivo or in vitro. Such scaffolds are suitably prepared in vitro and are then implanted in the site where rapid mineralization is required. Alternatively, such scaffolds are suitably prepared and mineralized to bone in vitro and the mineralized scaffolds are then implanted in the site where said bone is required. Thus, a method of the present invention may be performed in connection to tissue engineering (TE) in order to enhance bone formation on an organic or inorganic scaffold. The principle of TE involves the isolation and culture of cells, and the seeding of the cultured cells onto a biological or artificial scaffold in vitro prior to transplantation of the seeded scaffold into the specific location of the body. The scaffold thereby serves as an attachment matrix and guides the cells during tissue formation or regeneration. The regeneration of the seeded cells into a tissue may take place prior, during or after the implantation. As suitable scaffold materials, both organic and inorganic materials, as well as combinations thereof may be used.

A method of the present invention for controlling the mineralization of an ECM, may therefore be used in connection with a method for preparing a rapidly mineralizable scaffold. Such a method may comprise providing a suitable scaffold, seeding said scaffold with ECM-producing cells such as osteoblasts or progenitor cells thereof, such as stem cells. Stem cells may for instance be isolated from autologous sources (subject's bone marrow) and expanded in in vitro culture. Preferred progenitor cells are mesenchymal stem cells (MSC) which can be derived from various sources, including adipose tissue,. bone marrow, heart muscle etc. These progenitor cells can be induced by specific bioactive molecules to mature into a required cell type. MSCs may for instance be induced by dexamethasone to form osteoblasts. For bone (re)generation, mesenchymal stem cells may be induced into osteoblasts in vitro, for instance by using dexamethasone. For instance, MSCs may be directed by bone morphogenetic proteins (BMPs) to multiply and become specialized cells that produce cartilage (chondrocytes) or bone (osteoblasts). The osteoblasts may be subjected to an additional culture period, for instance for about 1-30 days, preferably for about 1-2 weeks in order to further expand such cells. Suitable culture media are known to the skilled person and may for instance comprise glycerophosphate and ascorbic acid. In order to induce in vitro osteogenic differentiation of human MSCs a suitable medium may comprise 1 to 1000 nM dexamethasone (Dex), 0.01 to 4 mM L-ascorbic acid-2-phosphate (AsAP) or 0.25 mM ascorbic acid, and 1 to 10 mM beta-glycerophosphate (beta GP).

A method of the present invention for controlling the mineralization of an ECM, may also be used in connection with a method for preparing a non-mineralizable scaffold or a scaffold wherein the mineralization is greatly reduced. Such scaffolds are for instance of great interest to serve as a scaffold for chondrocytes in cartilage tissue engineering and cartilage regeneration applications.

The cells may then be allowed to form an ECM in tissue culture or after being loaded onto a scaffold, for instance by using the medium described in the Example described below as used for SV-HFO osteoblast or NHOst osteoblast. Optimal osteogenic differentiation, as determined by osteoblastic morphology, expression of alkaline phosphatase (APase), collagen type I expression, osteocalcin expression and/or mineralization of the ECM or other osteoblast differentiation markers, may for instance be achieved using the medium described in the Example below as used for SV-HFO osteoblast or NHOst osteoblast. In a method of the invention for producing the mineralizable ECM, the osteoblasts are exposed to an activin-A inhibitor. Prior or subsequent to said exposure to the activin-A inhibitor, the osteoblasts may be seeded onto a scaffold, to produce the extracellular matrix. Alternatively, the progenitor cells may be seeded onto a scaffold and then induced to form osteoblasts, which are subsequently exposed to an activin-A inhibitor.

In a still further alternative, the osteoblasts may be exposed to an activin-A inhibitor, and allowed to produce the (preferably mature) ECM, and the ECM, either alone, or in combination with the osteoblasts, is then provided on the scaffold. Thus, the ECM may also be isolated from the osteoblasts and used as a matrix for rapid mineralization. In a preferred in vitro embodiment, the cells are seeded onto a scaffold and exposed to an activin-A inhibitor. In addition, the cells can be induced by yet other specific bioactive molecules such as growth factors, by ex-vivo gene transfer or by other physical factors to form the required neotissue in vitro. Alternatively, the scaffold may comprise growth factors. The in vitro prepared and loaded scaffold may then be implanted in a bone defect where the seeded cells are induced to mineralize the ECM. Of course, tissues or organs may also be produced completely in vitro and transplanted as ready replacement materials.

A method for controlling ECM mineralization according to the present invention may be used in various tissue-regeneration applications. For instance, a method of the present invention may be applied in defects relating to osteoporosis, trauma, orthopedy, tumoral cavities, Ear Nose & Throat, maxillo-facial surgery, peridontal surgery, fractures with bone defects, pseudarthrosis with or without bone defects, vertebral arthrodesis (spinal fusion), tibial osteotomy and/or heart valve transplantion. Other TE applications may include repair of e.g. bone. In the bone fracture-healing pathway, chondrocytes produce a cartilage framework that is eventually replaced with bone formed by the osteoblasts. Also here, the methods of the present invention can be applied.

The method of the present invention relates to the ECM of any cell capable of producing an ECM wherein mineralization of the ECM is required, especially the ECM of a cell of a patient in need of enhanced ECM mineralization. Exemplary ECMs are those of osteoblasts or chondrocytes during osteoporosis, fracture healing or bone remodelling. Also the method of the present invention relates the ECM of any cell capable of producing an ECM wherein mineralization of the ECM occurs but is undesirable, especially the ECM of a cell of a patient in need of reduction or prevention of ECM mineralization. Exemplary ECMs are those of vascular smooth muscle cells during or prior to atherosclerotic calcification. Thus, in one preferred embodiment, the mineralization relates to bone mineralization, while in another preferred embodiment, the mineralization relates to atherosclerotic calcification.

The methods of the present invention may be performed in vivo or in vitro. When performed in vitro, the method may for instance involve the control of the mineralization process associated with tissue cultures comprising excreted ECM, or associated with isolated ECM in a non-cellular environment. Very suitably, an in vitro method of the present invention is used to control the mineralization associated with tissue engineering or tissue-regeneration processes, such as mineralization in a bone repair implant.

When performed in vivo, the method may for instance involve the control of the mineralization process associated with bone fracture healing, or the treatment of osteoporosis. Alternatively, when performed in vivo, the method may for instance involve the control of the mineralization process associated with atherosclerotic calcification.

The present invention now provides in vivo or an in vitro methods for controlling the mineralization of an extracellular matrix of a cell involved in pathological calcification processes, including but not limited to atherosclerotic calcification, metastatic pulmonary calcification, heart valve calcification, and the calcifications in the joints associated with tendonitis; arthritis; bursitis; bone spurs; cutaneous ossification; kidney stones; myositis ossificans; pulmonary ossification; cataracts; bilateral striopallidodentate calcinosis; neurogenic heterotopic ossification and osteosarcoma; or for controlling the mineralization of an extracellular matrix of a cell involved in physiological calcification processes (e.g. ossification and bone mineralization), including but not limited to bone healing or bone formation and disorders therein such as osteoporosis. Such methods may relate to methods of medical treatment or to methods of medical engineering, such as tissue engineering.

Controlling the mineralization of an extracellular matrix of a cell involved in pathological calcification, including but not limited to a vascular cell, preferably a vascular smooth muscle cell, or a chondrocyte, will involve inhibiting or preventing mineralization of said extracellular matrix, in either of the following ways:

i) activating an activin receptor, preferably the type-II activin receptor, on the surface of a cell that produces the extracellular matrix. This can for instance be achieved by using a ligand or a functional analogue, an inducer and/or an agonists of said receptor. The ligand is preferably activin A, most preferably exogenous activin A; or ii) enhancing in said cell the expression of at least one gene selected from the group consisting of thrombospondin 1; collagen type V alpha 1; collagen type XVI alpha 1; collagen type VIII alpha 2; collagen triple helix repeat containing 1; hyaluronan and proteoglycan link protein 1; chondroitin sulfate proteoglycan 2 (versican); latent transforming growth factor beta binding protein 2; biglycan; matrix metallopeptidase 2; periostin, osteoblast specific factor; fibulin 5; SPOCK1, Sparc/osteonectin, cwcv and kazal-like domains proteoglycan (testican); and ADAM metallopeptidase with thrombospondin type 1 motif, or controlling the activity of an expression product of said gene; or iii) blocking or inhibiting in said cell the expression of at least one gene selected from the group consisting of CD248 antigen, endosialin; elastin microfibril interfacer 2; matrilin 2; dystrobrevin, alpha; collagen, type IV, alpha 6; nidogen 2 (osteonidogen); papilin, proteoglycon-like sulfated glycoprotein; C-type lectin domain family 3, member B; collagen type V, alpha 3; and TIMP metallopepetidase inhibitor 4, or controlling the activity of an expression product of said gene.

Controlling the mineralization of an extracellular matrix of a cell involved in physiological calcification, including but not limited to an osteoblast, will involve stimulating mineralization of said extracellular matrix, in either of the following ways:

iv) preventing the interaction between an activin receptor, preferably the type-II activin receptor, on the surface of a cell that produces said extracellular matrix and the endogenous ligand of said receptor. This can for instance be achieved by using a ligand-inhibitor, an inducer of said ligand-inhibitor and/or an antagonist of said receptor. The ligand-inhibitor is preferably follistatin; or v) blocking or inhibiting in said cell the expression of at least one gene selected from the group consisting of thrombospondin 1; collagen type V alpha 1; collagen type XVI alpha 1; collagen type VIII alpha 2; collagen triple helix repeat containing 1; hyaluronan and proteoglycan link protein 1; chondroitin sulfate proteoglycan 2 (versican); latent transforming growth factor beta binding protein 2; biglycan; matrix metallopeptidase 2; periostin, osteoblast specific factor; fibulin 5; SPOCK1, Sparc/osteonectin, cwcv and kazal-like domains proteoglycan (testican); and ADAM metallopeptidase with thrombospondin type 1 motif, or controlling the activity of an expression product of said gene; or vi) enhancing or stimulating in said cell the expression of at least one gene selected from the group consisting of CD248 antigen, endosialin; elastin microfibril interfacer 2; matrilin 2; dystrobrevin, alpha; collagen, type IV, alpha 6; nidogen 2 (osteonidogen); papilin, proteoglycon-like sulfated glycoprotein; C-type lectin domain family 3, member B; collagen type V, alpha 3; and TIMP metallopepetidase inhibitor 4, or controlling the activity of an expression product of said gene.

The invention provides methods of medical treatment wherein the treatment comprises controlling the mineralization process of the extracellular matrix as described above. The method may be an in vivo or an in vitro method.

The invention thus provides a method for treating or preventing pathological calcifications, preferably a pathological calcification selected from the group consisting of atherosclerotic calcification, metastatic pulmonary calcification, heart valve calcification, and the calcifications in the joints associated with tendonitis; arthritis; bursitis; bone spurs; cutaneous ossification; kidney stones; myositis ossificans; pulmonary ossification; cataracts; bilateral striopallidodentate calcinosis; neurogenic heterotopic ossification and osteosarcoma, comprising controlling the mineralization of an extracellular matrix by a method of the invention according to embodiments i), ii) or iii) as described above.

The invention also provides a method for stimulating mineralization, bone healing, bone formation and/or for treating osteoporosis, comprising controlling the mineralization of an extracellular matrix by a method of the invention according to embodiments iv), v) or vi) as described above.

As products for use in such medical treatment, the present invention provides a medicament for the treatment of pathological calcifications, said medicament comprising an activin receptor ligand, or an agonist or functional analogue thereof, preferably activin-A, and a pharmaceutically acceptable vehicle. The present invention also provides a medicament for the treatment of osteoporosis or bone fractures, said medicament comprising an activin-A inhibitor, preferably follistatin, and a pharmaceutically acceptable vehicle.

The invention provides non-therapeutic methods, such as methods of medical engineering (preferably ex vivo), e.g. tissue engineering. In one embodiment of that aspect, the invention provides a method of producing a non-mineralizing extracellular matrix, comprising performing a method for inhibiting or preventing the mineralization of an extracellular matrix as described above and optionally isolating the extracellular matrix thus obtained. Such a matrix may for instance be used for the production of cartilage tissue. In an alternative embodiment of that aspect, the invention provides a method of producing a rapidly-mineralizing extracellular matrix, comprising performing a method for stimulating mineralization of said extracellular matrix as described above and optionally isolating the extracellular matrix thus obtained. Such a matrix may for instance be used for the production of bone tissue.

The present invention also provides a marker for diagnosing osteoporosis in a subject. The marker as proposed herein is the ratio of the amount of activin-A to the amount of follistatin secreted by osteoblasts in bone tissue of said subject. The skilled person is well acquainted with methods for determining the levels of such proteinaceous compounds in tissues. For instance, ELISA tests or mass-spectrometric assays may be used to determine the amounts (levels) of follistatin and activin A in bone tissues. The subject is diagnosed with osteoporosis when said ratio is elevated when compared to control subjects. This means that the tissue is not mineralizing or has a low potency of being mineralized as the ratio predicts that composition of the extracellular matrix is such that it remains immature.

By way of example, and not of limitation, Examples of the present invention will now be given.

EXAMPLE

The aim of the experiments described below was to assess the function of activins in human osteoblasts. Human osteoblasts were used that form a mineralized ECM in vitro, in which regulation of mineralization by activins was analyzed. Activin production during osteoblast differentiation was measured together with the expression of activin antagonists. Whole genome expression profiling was performed to reveal down-stream mediators of activin-signaling in osteoblasts. In addition, the effect of activins on vascular calcification was studied using human vascular smooth muscle cells (VSMCs).

Materials and Methods

Cell Culture

The culture protocol for cells of the immortalized human osteoblastic cell line SV-HFO established from fetal calvaria is described in detail in Eijken, M., et al. Mol Endocrinol, 2005. 19(3): p. 621-31. Briefly, SV-HFO cells between passage 9 and 13 were cultured in α-Minimal Essential Medium (Gibco BRL, Paisley, U.K.) supplemented with 20 mM HEPES pH 7.5 (Sigma St. Louis, Mich., U.S.A.), streptomycin/penicillin (Gibco BRL), 1.8 mM $CaCl_2$ (Sigma) and 2% charcoal-treated heat-inactivated fetal calf serum (FCS) (Gibco BRL) at 37° C. and 5% $CO_2$ in a humidified atmosphere. Cells were seeded in a density of $10 \times 10^3$ vital cells per $cm^2$ in 6- or 12-wells plates (Corning, N.Y., USA). After seeding, cells were incubated for two days before they were put on differentiating-mineralizing medium (α-Minimal Essential Medium supplemented with 20 mM HEPES pH 7.5, streptomycin/penicillin, 1.8 mM $CaCl_2$, and 2% charcoal-treated heat-inactivated FCS, 10 mM β-glycerophosphate and 100 nM dexamethasone) (indicated as day 0). Medium was supplemented with freshly added 10 mM (β-glycerophosphate (Sigma), 100 nM dexamethasone (DEX) (Sigma) or other additives (activin and follistatin) and replaced every 2-3 days. Follistatin was purchased from PeproTech (Rocky Hill, N.J., USA) and activin A from R&D systems (Minneapolis, Minn., USA).

Normal human osteoblasts (NHOst) (Cambrex Bio Science, Verviers, Belgium; CC-2538), vascular smooth muscle cells (VSMCs) (Coronary artery smooth muscle cells; Cambrex bioscience; CC-2583) and human mesenchymal stem cells (hMSC); (Cambrex bioscience) were cultured similar to SV-HFO cells as described above only with the following adjustments. NHOst and hMSC were used between passage 3 and 6 and were seeded in a density of $5 \times 10^3$ vital cells per $cm^2$. NHOst and hMSC cultures were induced to mineralize in similar medium as SV-HFO, except that 10% charcoal-treated heat-inactivated FCS (Gibco BRL) was used. VSMCs were used between passage 3 and 7 and seeded in a density of $5 \times 10^3$ vital cells per $cm^2$. Expansion of VSMCs was performed in smooth muscle cell medium (Cambrex Bio Science) supplemented with Clonetics™ Sm-GM-2 Bulletkit (Cambrex Bio Science). VSMCs were induced to mineralize in Dulbecco's Modified Eagle's Medium (DMEM) (Gibco BRL; with 4500 mg/l glucose, L-glutamine and pyruvate) supplemented with 100 nM DEX, 0.1 mM ascorbic acid (Sigma), 10 μg/ml insulin (Sigma), 1 mM $CaCl_2$ (final concentration of 2.8 mM), 10 mM β-glycerophosphate and 10% FCS.

Devitalization of Osteoblast Cultures

At day 12 of cultivation in mineralizing medium culture medium was removed and the cultures were washed once in phosphate-buffered saline (PBS) (Gibco BRL). Cultures were air dried and incubated overnight at −20° C. Next, the devitalized cultures were incubated normally as described in the cell culture methods (indicated as day 0 for devitalized cultures).

DNA, Alkaline Phosphatase Activity and Mineralization Assays

Cell Cultures were Scraped from the Culture Dish in Pbs Containing 0.1% Triton X-100 and stored at −80° C. Prior to analysis cell-lysates were sonicated on ice in a sonifier cell disrupter for 2×15 seconds and used for the DNA, alkaline phosphatase activity and mineralization assays, which are described in detail in Eijken et al., 2005 [supra] which reference is incorporated herein in its entirety. Shortly, DNA content was measured fluorimetrically using ethidium bromide solution. Alkaline phosphatase activity was measured by determining the release of paranitrophenol from paranitrophenylphosphate. Calcium content was determined colorimetrically after addition of 1M ethanolamine buffer (pH 10.6) 0.35 mM o-cresolphthalein complexone, 19.8 mM 8-hydroxyquinoline and 0.6 mM hydrochloric acid at 595 nm. For Alizarin Red staining cell cultures were fixed for 60 min with 70% ethanol on ice. After fixation, cells were washed twice with PBS and stained for 10 min with Alizarin Red solution (saturated Alizarin Red in dematerialized water adjusted to pH 4.2 using 0.5% ammonium hydroxide). Alizarin Red S was removed and cultures were washed with demineralized water.

Luciferase Reporter Assays

At day 5 of culture cells were transfected with 200 ng reporter plasmids per well (12 wells plate) using Fugene6 (Roche, Basel, Switzerland) according to the manufacturer's description. After 24 hours medium was replaced by fresh medium containing low serum (0.2% FCS) and incubated for 3 hours. After 3 h medium was refreshed for the second time with medium containing low serum, however now supplemented with additives described in the results section. After 24 hours cells were lysed by incubating for 20 minutes in 100-200 μl lysis buffer (Promega, Madison, Wis.). Luciferase activity was measured using 25 μl cell-lysate and the Steady-Glo Luciferase Assay System (Promega). Activin signaling was measured using pGL3(CAGA)12-lux (GAGA-Luc) (Dennler et al, Embo J, 1998 17: 3091-100) and BMP signaling was measured using pGL3-BRE-luc (BRE-Luc) (Korchynskyi et al. J Biol Chem, 2002. 277: 4883-91.

Quantification of Follistatin and Activin-A

At various days during culture medium was collected for activin-A and follistatin measurements. Medium was collected from the cultures after 48 h incubation. Medium was centrifuged (5 min, 500 g) and subsequently stored at −20° C. for further analysis. Cell lysates were also prepared to analyze DNA content of the corresponding cultures. To quantify activin-A and follistatin an amount of 100 μl of medium was analyzed using an activin-A DuoSet ELISA kit or follistatin quantikine ELISA kit (R & D systems), respectively.

Immunohistology

Plastified bone sections were deacrylated in a 1:1 mixture of xylene and chloroform for 30 minutes, then dipped in xylene, rehydrated and rinsed twice with distilled water.

Slides were pretreated with Tris-EDTA Buffer pH 9.0 for 15 minutes at 100° C. and cooled down for 15 minutes followed by rinsing in running tapwater. Endogenous peroxidase activity was inhibited by a 10:1 mixture of PBS and $H_2O_2$ for 10 minutes, followed by two water washes and one Tris-HCl pH 8.0 wash. The following steps were carried out in a humidified chamber at room temperature. Primary antibodies were diluted 1:50 in normal antibody diluent (Skytek Laboratories, UT, USA; ref. ABB999) and incubated for 60 minutes. Inhibin-βA, Inhibin-α and IgG2b negative control antibody were purchased from Serotec (Serotec, Oxford, UK; MCA950 ST, MSA951S, MCA691). Slides were rinsed in two Tris-HCl. Slides were detected with Dako REAL™ Envision™ Detection System, Peroxidase/DAB+, Rabbit/Mouse (Dako, Glostrup, Denmark; Code K5007). After DAB detection slides were rinsed in running tap water, and counterstained in Harris Haematoxylin for 1 minute, rinsed in running tap water for 2 minutes, dehydrated in ascending ethanol steps. Rinsed in xylene and covered with a cover slip using Pertex mounting medium (Histolab, Gothenburg, Sweden).

Real-time PCR Analysis (qPCR)

RNA isolation, cDNA synthesis and qPCR are described in detail in Eijken et al., 2005 [supra]. Briefly, quantitative realtime reverse transcription PCR (qPCR) was carried out using an ABI 7700 sequence detection system (Applied Biosystems, Foster City, Calif., USA). Gene expression was quantified using SYBR green or a fluorescent internal probe (5'-FAM; 3'-TAMRA). For the SYBR green and fluorescent probe assay the PCR reactions contained 20 ng of cDNA and were performed using a qPCR kit for SYBR green I or qPCR core kit (Eurogentec), respectively. The amount of human glyceraldehyde-3-phosphate dehydrogenase mRNA (GAPDH) was used as internal control to normalize for possible differences in RNA extraction and degradation as well as efficiency of the cDNA synthesis. Data were presented as relative mRNA levels calculated by the equation $2^{-\Delta Ct}$ ($\Delta Ct=Ct$ of target gene minus Ct of GAPDH). For qPCR analysis RNA was used isolated from cultures, which were not used for the micro-array analysis.

Affymetrix Array-based Gene Expression

Purity and quality of isolated RNA was assessed by RNA 6000 Nano assay on a 2100 Bioanalyzer (Agilent Technologies). None of the used samples showed significant degradation or DNA contamination. Per analyzed condition total RNA was pooled of 3 different samples. Synthesis of first and second strand cDNA from total RNA was performed according to the One-Cycle Target Labeling protocol (Affymetrix; 701024 Rev. 3). In total, 4.0 μg of total RNA was reverse transcribed using Superscript ds-cDNA Synthesis Kit according to the manufacturer's description (Invitrogen). Subsequently, double-stranded cDNA was purified using GeneChip Sample Cleanup Module (Affymetrix) and served as a template in the in vitro transcription reaction using BioArray™ HighYield™ RNA Transcript Labeling Kit (Affymetrix). The amplified biotinylated complementary RNA (cRNA) was purified using GeneChip Sample Cleanup Module and quantified spectrophotometrically (1 OD260 nm=40 μg/mL). In total, 20 μg of biotin-labeled cRNA was fragmentized by metal-induced hydrolysis at a final concentration of 0.5 μg/μL for 35 minutes at 94° C. Fragmentation was checked on an Agilent 2100 Bioanalyzer confirming an average size of approximately 100 nt. In total, 15 μg fragmented biotinylated cRNA was hybridized to GeneChip Human Genome U133 Plus 2.0 oligonucleotide microarrays (Affymetrix) according to the manufacturer's protocol (Affymetrix, 701025 Rev 5). Staining, washing and scanning procedures were carried out as described in the GeneChip Expression Analysis technical manual (Affymetrix). Data acquisition was performed in about 12 minutes per array using the GeneChip(r) Scanner 3000.

Micro-array Data Analysis

In order to examine the quality of the different arrays, measured intensity values were analysed using the GeneChip Operating Software (GCOS, Affymetrix). Percentage of present calls (about 40%), noise, background, and ratio of GAPDH 3' to 5' (<1.4) all indicated high quality of samples and an overall comparability.

Probe sets that were never present (according to Affymetrix MAS5.0 software) in any of the microarrays were omitted from further analysis. Raw intensities of the remaining probesets (30336) of each chip were log 2 transformed and normalized using quantile normalization. After normalization the data was back transformed to normal intensity values. Data analysis was carried out using the OmniViz software, version 3.6.0 (OmniViz, Maynard, Mass.).

Gene Nomenclature

Gene names and gene symbols were used as provided by HUGO Gene Nomenclature Committee [Wain, H. M., et al., Guidelines for human gene nomenclature. Genomics, 2002. 79(4): p. 464-70].

Statistics

Data were only presented if multiple independent experiments showed similar results. Experiments were performed at least in triplicate. Values are the means±SEM. Significance was calculated using the Student's t-Test. To calculate significance for the GO analyses Benjamini and Hochberg false discovery rate was used [Young, A., et al., OntologyTraverser: an R package for GO analysis. Bioinformatics, 2005. 21(2): p. 275-6].

Results

Activin-A Inhibits Mineralization in Human Osteoblast Cultures

Figure 6:
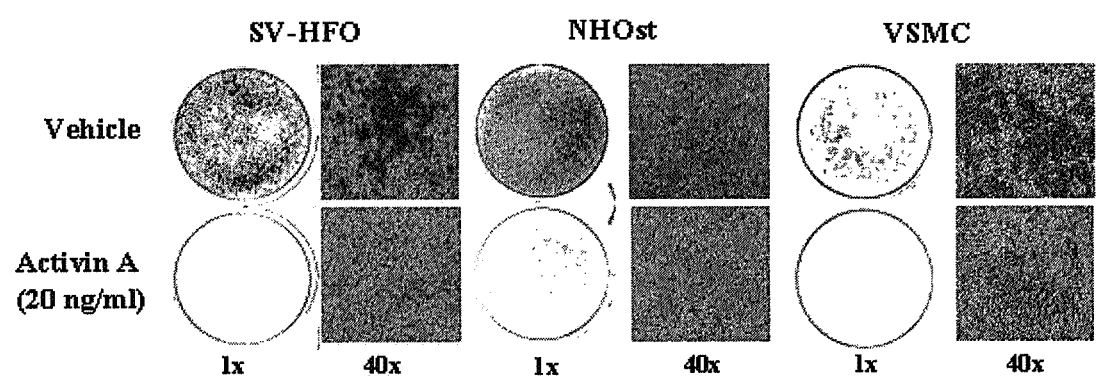
FIG. 6 shows the inhibition of mineralization by activin-A in osteoblasts and vascular smooth muscle cells. Two different osteoblast differentiation models (SV-HFO and NHOst) and vascular smooth muscle cells (VSMCs) were induced to mineralize in the absence (top row) and continuous presence (bottom row) of activin-A (20 ng/ml). Mineralization was visualized by Alizarin Red S staining at day 14 for SVHFO cultures and NHOst cultures and at day 30 of culture for VSMC using microscopic observation at 1× and 40× magnification. Induction of mineralization in the absence of activin-A resulted in thorough Alizarin Red S staining indicative of the presence of calcium in the matrix (top row), whereas induction of mineralization in the presence of activin-A resulted in virtually no staining (bottom row).

The role of activin-signaling in osteoblasts was studied in detail using the osteoblast differentiation model SV-HFO. This human osteoblast model produces an extracellular matrix (ECM) during culture, which is eventually mineralized in a 2 to 3 week time period. Using these human osteoblasts we demonstrated that activin-A treatment strongly inhibited the mineralization process (FIG. 1 and FIG. 6). This effect was dose-dependent showing significant reduction of the mineralization after treatment with activin-A concentrations higher then 5 ng/ml. Also the osteoblast differentiation marker alkaline phosphatase (ALPL) was dose-dependently decreased by activin-A (data not shown), however, the magnitude of inhibition (10-30%) was smaller compared to that of mineralization. Activin-A treatment had no effect on cell growth as demonstrated by unchanged DNA content (data not shown).

Osteoblasts Produce Activin-A in a Differentiation Dependent-manner

Figure 2:
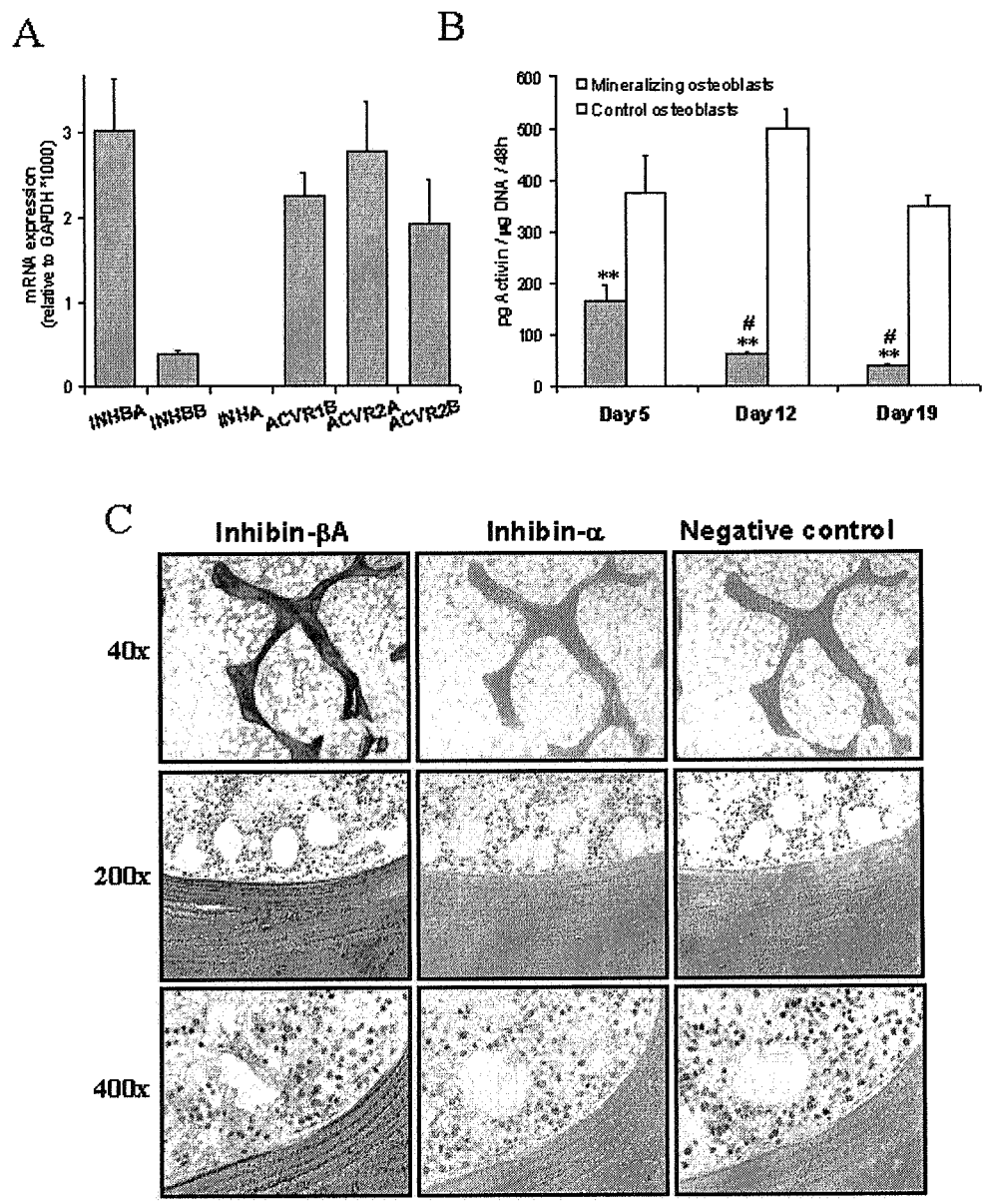
FIG. 2 shows the production and localization of activin-A in human bone tissue. (A) Expression (mRNA) of inhibin/activin subunits and activin type I and type II receptors in osteoblast (SV-HFO) cultures. (B) Production of activin-A protein by human osteoblasts (SVHFO). Activin-A levels were measured in the culture supernatant of control-osteoblast cultures and osteoblast cultures that were induced to mineralize. Production was corrected for the culture DNA content. * $p<0.05$; ** $p<0.01$ compared to control-cultures; #$p<0.01$ compared to day 5 of mineralizing-cultures. (C) Immunohistological staining of Inhibinβ A (INHBA) (left panels; strong brown (dark) coloration) and Inhibin α (INHA) (centre panels; no coloration at all) in human bone tissue. Mouse IgG2b used as a negative control (right panels; slight coloration), this antibody does not react with any human cell surface marker.

To reveal if activin acts in an autocrine manner we measured the mRNA levels of the two inhibin-β subunits together with activin-A protein in human osteoblasts. QPCR demonstrated that inhibin-βA (INHBA) was abundantly expressed compared to the inhibin-βB (INHBB) subunit. Inhibin-a (INHA) mRNA on the other hand was almost undetectable (FIG. 2A). This suggests that osteoblasts mainly produce activin-A.

Quantitative activin-A protein measurements showed that osteoblast cultures secrete biological relevant amounts of activin-A (up to 5 ng/ml), whereas inhibin-A protein could not be detected (data not shown). Activin-A production corrected for cell number (DNA content) was measured at different stages of differentiation (day 5, 12 and 19). This showed that activin-A production decreased during differentiation and was lowest during stages of matrix mineralization (day 12 and 19) (FIG. 2B, mineralizing osteoblasts).

To explore this differentiation dependent regulation, activin-A production was measured in osteoblast cultures that do not undergo differentiation. Non-differentiating osteoblasts (control osteoblasts) were created by excluding glucocorticoids (DEX) from the culture medium, resulting in osteoblast cultures having low ALP activity and exhibiting no in vitro mineralization. Interestingly, control osteoblasts had much higher activin-A production compared to their mineralizing counterparts (FIG. 2B), demonstrating that mature functional osteoblasts have suppressed activin-A production.

In addition, immunohistochemistry on human bone biopsies showed that human bone tissue was loaded with activin-A. The INHBA subunit was clearly detected in mineralized bone matrix whereas the INHA subunit could not be detected (FIG. 2C).

Activin-A Inhibits Mineralization in an Autocrine Manner

Figure 3:
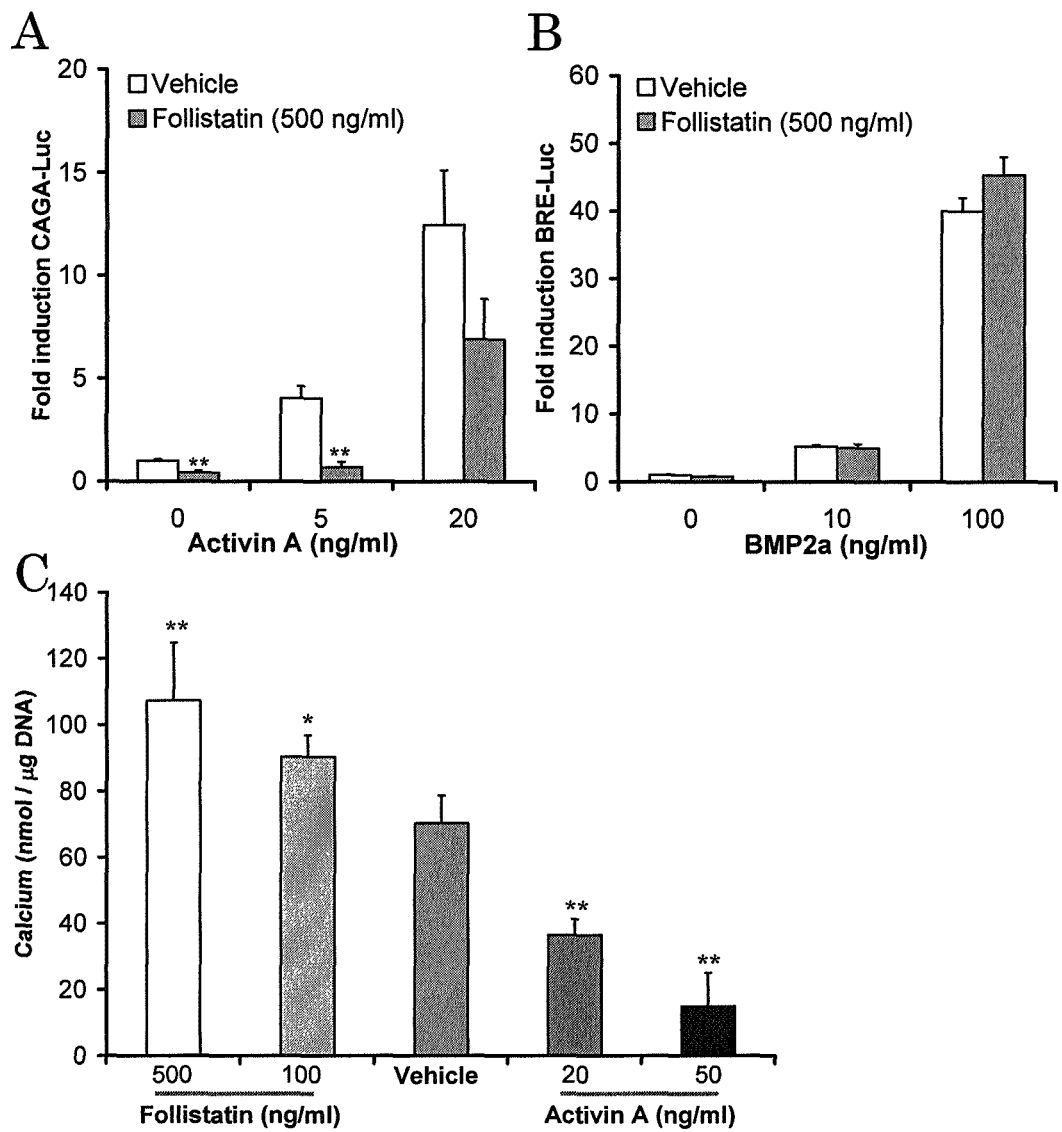
FIG. 3 shows the inhibition of endogenous activin-signaling by follistatin in osteoblast cultures (SV-HFO). Panel (A) shows the induction of an activin responsive reporter construct (CAGA-luciferase) in response to various activin A concentrations (0, 5 and 20 ng/ml of cell culture) in the absence (vehicle) and presence of 500 ng/ml follistatin (24 h after the onset of the treatment). Follistatin clearly reduces the level of the luciferase assay. (B) Similar as (A) only a BMP-responsive reporter construct was used (BRE-luciferase) and cultures were treated with BMP-2a instead of activin-A, optionally in combination with follistatin. Clearly, no effect of follistatin is observed. (C) Osteoblast cultures were treated with follistatin or activin-A for 19 days and the calcium content was measured at day 19. * $p<0.05$; ** 0.01 compared to vehicle.

The impact of endogenously produced activins on osteoblast-function was measured by neutralizing activin-signaling by the activin antagonist follistatin. First we measured whether follistatin was capable of neutralizing activin-signaling in osteoblast cultures. An activin/TGFβ signaling luciferase reporter construct (CAGA-luciferase) was used to measure activin-signaling. Activin-A treatment dose-dependently increased activin/TGFβ signaling, which could be inhibited by co-incubation with follistatin (FIG. 3A). Moreover, follistatin also reduced basal activin/TGFβ signaling by 50%, which further supports the observation of endogenous activin signaling in osteoblasts. It is suggested in the literature that follistatin also neutralizes BMP action. To study this in osteoblasts a BMP-responsive element luciferase reporter construct was used (BRE-luciferase). Addition of 10 and 100 ng/ml BMP-2a strongly induced BRE luciferase activity. In contrast to activin-signaling both basal and BMP-2a induced BMP signaling could not be reduced by the presence of follistatin (FIG. 3B). This showed that under these conditions follistatin specifically neutralizes activin-signaling in osteoblasts. This inhibitory effect of follistatin was used to study the impact of endogenous activin-signaling on osteoblast differentiation and mineralization. Treatment with follistatin (100 and 500 ng/ml) clearly increased matrix mineralization (FIG. 3C) together with a minor increase in ALP activity (data not shown). This demonstrated that osteoblasts secrete activin-A that inhibits mineralization and ALP activity in a para- and/or autocrine way.

Activin-A to Follistatin Ratio is Decreased in Mineralizing Cultures

Figure 4:
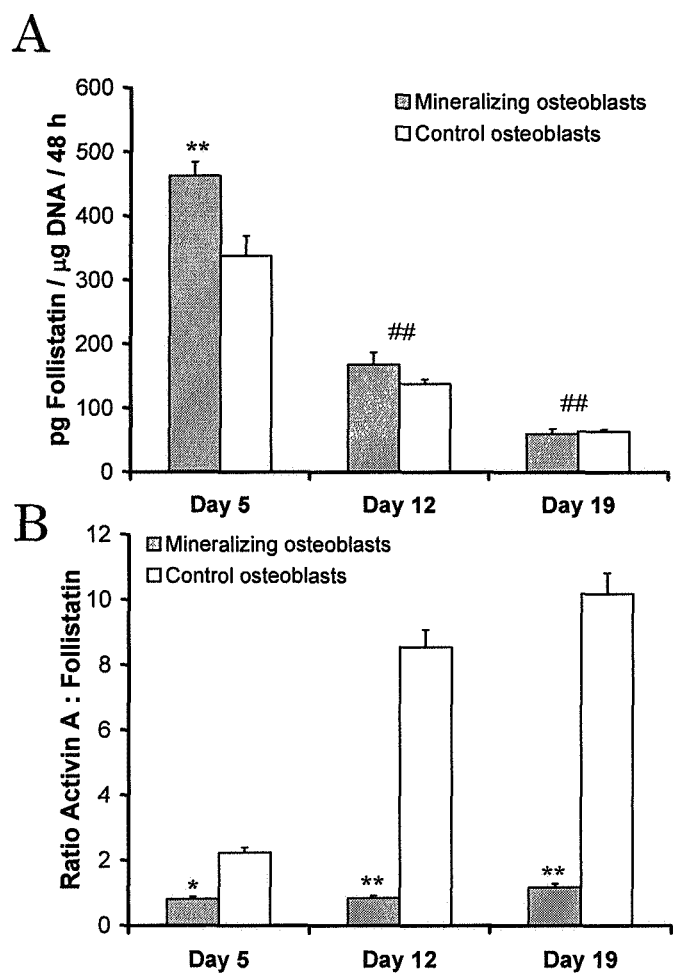
FIG. 4 shows the quantitative relationship between activin-A and follistatin. (A) Follistatin production by human osteoblasts (SV-HFO) at day 5, 12 and 19 in control and mineralizing conditions. (B) Activin-A and follistatin concentrations were measured in the culture supernatant of control- and mineralizing-osteoblasts at day 5, 12 and 19 subsequent the molar ratio between activin-A and follistatin was calculated. * $p<0.05$; ** $p<0.01$ compared to control-osteoblasts.

Apart from activin-A production by osteoblasts we also demonstrated that osteoblasts secrete biological relevant amounts of follistatin. At day 12 of culture maximum levels of follistatin could be measured of 1-3 ng/ml in the cultures supernatant after 2 days of medium incubation (data not shown). This indicates that in osteoblasts endogenous activin-signaling is regulated by expression of activin-A as well as expression of F follistatin. The production of follistatin was calculated (follistatin levels corrected for cultures DNA content) throughout culture in mineralizing- and control-osteoblasts (FIG. 4A). This showed that follistatin production was higher at the beginning of culture (day 5) in mineralizing-osteoblast compared to control-osteoblasts and that follistatin production decreased during culture in both conditions. Next, the molar ratio between activin-A and follistatin was calculated. This showed that mineralizing-cultures have a reduced activin-A to follistatin ratio compared to control-cultures, indicating suppressed activin-signaling in mineralizing conditions (FIG. 4B).

Activin-signaling is Most Effective Prior to the Onset of Mineralization

Figure 5:
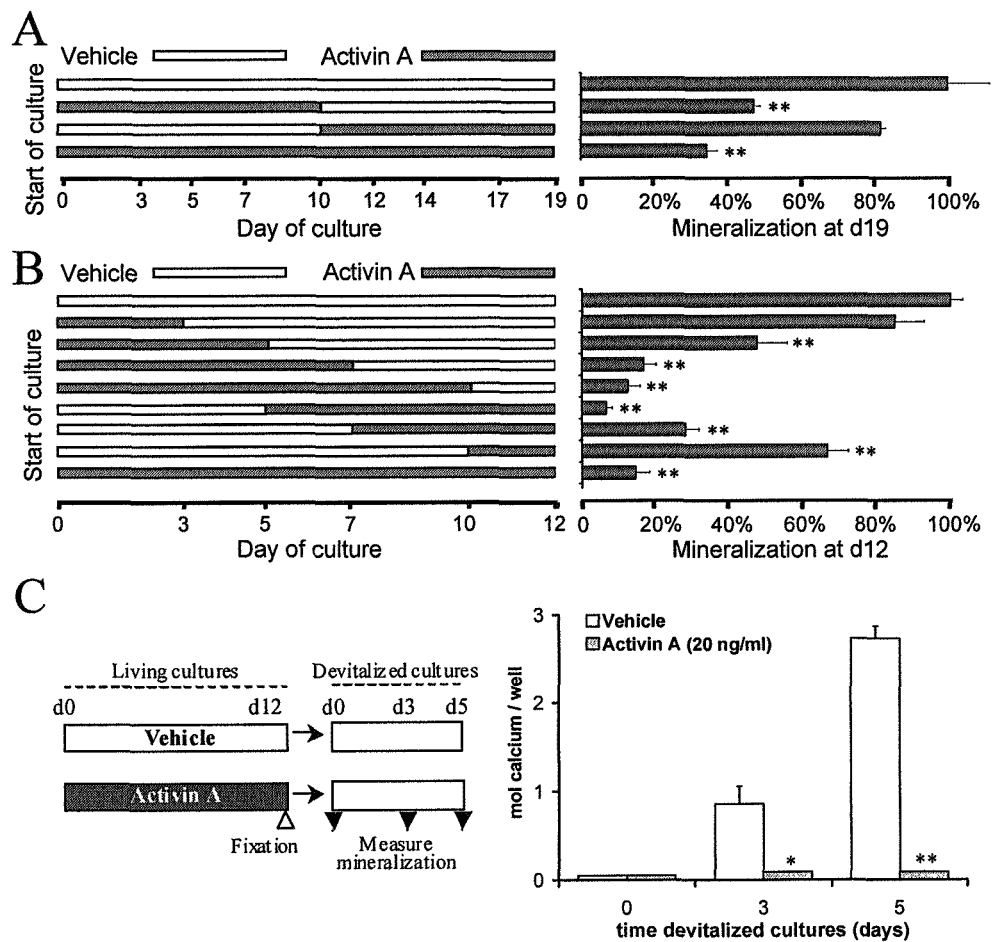
FIG. 5 exemplifies the time specific effect of activin signaling. (A) Osteoblasts (SV-HFO) were treated with activin-A prior to the onset of mineralization (day 0 to 10), after the onset of mineralization (day 10 to 19), during the whole culture period (day 0 to day 19) or non-treated. At the end of culture (day 19) calcium content was measured. (B) Osteoblasts (SV-HFO) were treated with activin-A in specific time-period prior to the onset of mineralization. Calcium content was measured at day 12. (C) Osteoblast cultures (SV-HFO) were cultured for 12 days in the presence or absence of activin-A. At day 12, cultures were fixed and killed by freezing and subsequently cultured in normal culture medium. At the moment of fixation and after 3 and 7 days of fixation calcium content was measured. ** $p<0.01$ compared non-treated cultures.

We investigated whether activin-signaling inhibits mineralization during a specific time-window of osteoblast differentiation. Several incubation protocols were used in which osteoblast cultures were treated with activin-A during specific time-periods. First, cultures were treated during the pre-mineralization period (up to day 10 of culture) or during the mineralization period (from day 10 of culture onwards) with a moderate-dose activin-A (20 ng/ml) and subsequent mineralization was measured at day 19 (FIG. 5A). This showed that treatment preceding the mineralization period was most effective to inhibit mineralization. To zoom in on this pre-mineralization period more specific incubations were performed as depicted in FIG. 5B. This showed that activin-A was most effective when present in the final 7 days prior to the onset of mineralization. Even when activin-A was only present during the final two days (day 10-12) before mineralization a significant decrease in mineralization was measured.

We hypothesized that activin-signaling in this pre-mineralization phase leads to an altered matrix composition, keeping it in an immature state not capable to mineralize. To prove this we exploited the fact that osteoblasts produce an ECM within the first 12 days of culture that can subsequently mineralize independent of further presence of living osteoblasts (FIG. 5C, vehicle) (Fratzl-Zelman, N., et al., Matrix mineralization in MC3T3-E1 cell cultures initiated by beta-glycerophosphate pulse. Bone, 1998. 23(6): p. 511-20). This was achieved by freezing osteoblast cultures to −20° C. (to devitalize the culture) at the onset of mineralization (day 12). Next, these cultures containing non-living cells but an intact ECM were subsequently incubated for 7 additional days with culture medium. Mineralization was quantified at the moment of fixation (day 12 living cultures=day 0 devitalized cultures) and after 3 and 7 days (see incubation scheme FIG. 5C). No mineralization was measured at the beginning (day 0), however, after 3 and 7 days mineralization of the ECM could be measured (FIG. 5C, vehicle). Importantly, in cultures that were pre-treated with activin-A prior to devitalization no mineralization of the ECM could be detected. This supports our hypothesis that the major impact of activin-A is prior to the onset of mineralization and suggests an effect on matrix composition and maturation.

Activin Suppresses Osteoblastic Mineralization as Well Ectopic Mineralization

Different mineralization-models were treated with activin-A to demonstrate that inhibition of mineralization induced by activin-A was not unique for the SV-HFO human osteoblasts model.

Activin-A was tested in another osteoblast model (NHOst) and in vascular smooth muscle cell (VSMCs) cultures. These VSMCs are used as a model for atherosclerosis [Shioi, A., et al. Arterioscler Thromb Vasc Biol, 1995. 15(11): p. 2003-9] and can be induced to mineralize using an osteogenic medium. As demonstrated for SV-HFO cultures, activin type-I (ACVRIB) and type-II receptors (ACVR2A/2B) were expressed (mRNA) in NHOst as well as in VSMC cultures (data not shown). Importantly, activin-A strongly inhibited the mineralization process in both NHOst and VSMC cultures (FIG. 6).

Gene Profile Analysis of Follistatin and Activin-A Treated Cultures

Gene profile experiments were performed to gain insight into the mechanism and molecular action of activin-A in osteoblasts using Affymetrix HG U133 Plus 2.0 micro-arrays. Gene expression profiles of follistatin-, vehicle- and activin-A-treated osteoblasts were compared. These treatments created cultures having low-, moderate (endogenous)-, or high activin-signaling, resulting in 3 different levels of matrix mineralization as demonstrated in FIG. 3C. Furthermore, gene expression was measured at 3 phenotypically different stages; 1) matrix formation, no mineralization (day 5), 2) matrix maturation, onset mineralization (day 12), and 3) full mineralization (day 19).

Figure 7:
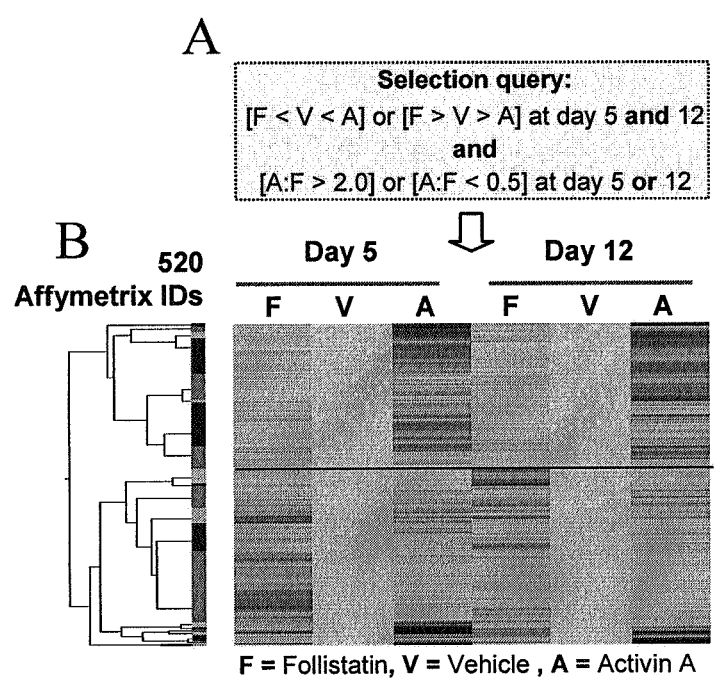
FIG. 7 shows the identification of genes regulated by activin-signaling. The figure is a grey-scale of an original color scheme. (A) Phenotype based selection query based on Affymetrix expression microarray data of vehicle, activin A (50 ng/ml) and follistatin (500 ng/ml) treated osteoblast cultures (SV-HFO). Genes were selected that were up-regulated in activin A-treated cultures (low mineralization) and at the same moment were down-regulated in follistatin-treated cultures (high mineralization) compared to vehicle cultures or vice versa both at day 5 and 12. In addition, the difference in gene expression between activin A and follistatin treated cultures should at least be 2-fold at one of these two days (B) Hierarchical clustering of 520 Affymetrix probe sets that match this selection query representing 397 unique genes and 62 non-annotated probe sets. Red colors (top half Day 5 F, bottom half Day 5 "A", top half Day 12 "F" and bottom half Day 12 "A") indicate up-regulation and green colors (bottom half Day 5 F, top half Day 5 "A", bottom half Day 12 "F" and top half Day 12 "A") indicate down-regulation compared to vehicle cultures (V). Color intensities indicate the magnitude of regulation.

A phenotype-based query was designed that focused on genes regulated by activin signaling in the pre-mineralization period (day 5 and 12) which was shown to be important for inhibition of mineralization by activin-A. An important aspect in the selection query was that we searched for genes that were regulated in both follistatin and activin-A-treated cells, since both conditions affect mineralization. Genes were selected that were up-regulated in activin-A-treated cultures (low mineralization) and at the same moment down-regulated in follistatin-treated cultures (high mineralization) compared to vehicle cultures or vice versa both at day 5 and 12. In addition, the difference in gene expression between activin-A and follistatin treated cultures should at least be a factor-2 at one of these two days (FIG. 7). In total 520 Affymetrix IDs were selected representing 397 unique genes and 62 non-annotated Affymetrix IDs. The selected Affymetrix IDs are presented as a hierarchical clustering in FIG. 7; red and green colors indicate up- and down-regulation compared to vehicle cultures, respectively.

Gene Ontology (GO) Analysis

Next, GO enrichment analysis was used to categorize the 397 selected genes for the categories, GO Biological Process, GO Molecular Function, and GO Cellular Component (Data not shown) (Young, A., et al., OntologyTraverser: an R package for GO analysis. Bioinformatics, 2005. 21(2): p. 275-6). In total, we identified 47 biological processes, 13 molecular functions, and 4 cellular components as significantly over-represented (corrected for multiple testing) compared to what would be expected if 397 random genes were analyzed. Several biological processes GO terms shared high similarity and were identified by similar groups of genes.

Figure 8:
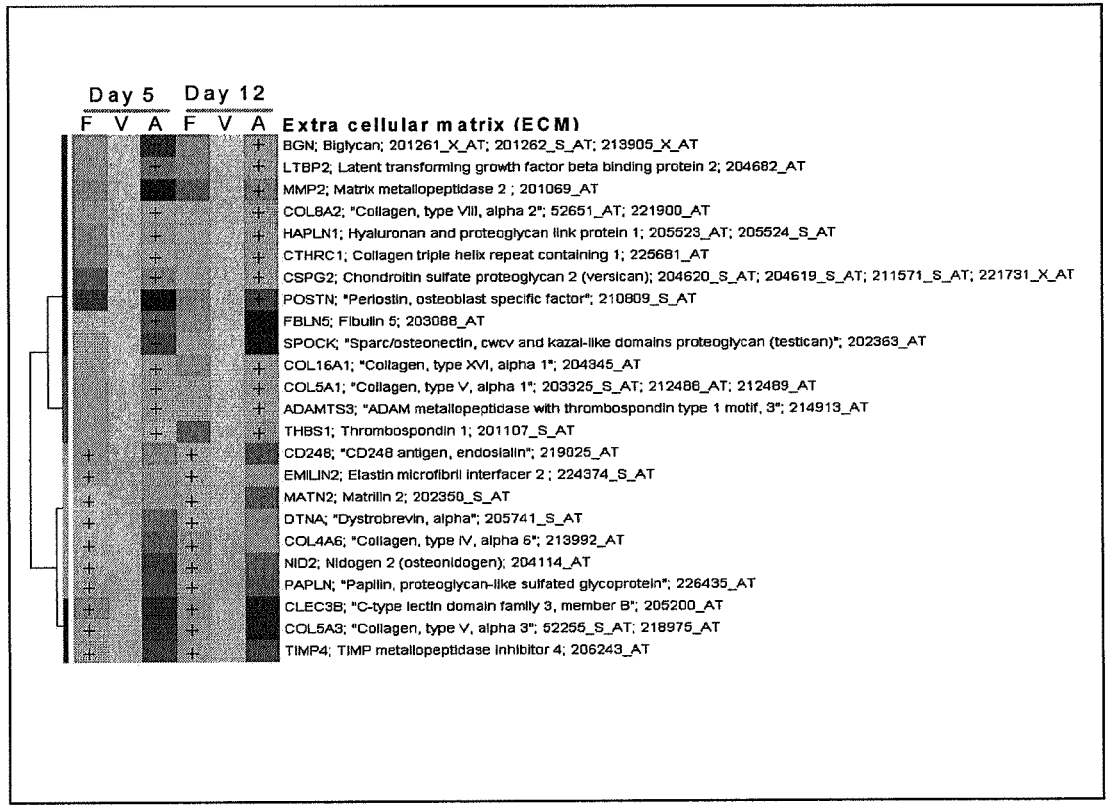
FIG. 8 shows the expression of genes localized in the extracellular matrix that are regulated by Activin-signaling. The figure is a grey-scale of an original color scheme. Provided is a hierarchical clustering of genes that matched the selection query (FIG. 7) and had an extracellular matrix (ECM) GO annotation. Official gene symbol, gene name and affymetrix probe sets are listed together with the gene regulation at day 5, and 12. Red colors (provided with a "+") indicate up-regulation and green colors (top part of "F" columns and bottom part of "A" columns) indicate down-regulation compared to control cultures (V).

The analysis for cellular component showed that genes located in the extracellular region, space or matrix were significantly over-represented. This is the more so interesting as this unbiased gene expression profiling and analyses support our hypothesis that activin-A effect is most important in the extracellular matrix formation and maturation period (see FIG. 5). qPCR analyses showed that mRNA expression of the well-known and abundant ECM proteins in bone; collagen type-I, osteopontin and osteocalcin were unchanged by activity signaling (data not shown). However, these micro-array analyses identified numerous genes located in the ECM that were regulated by activin-signaling (FIG. 8).

Activin Signaling Alters ECM Composition in Osteoblasts as well in VSMCs

Figure 9:
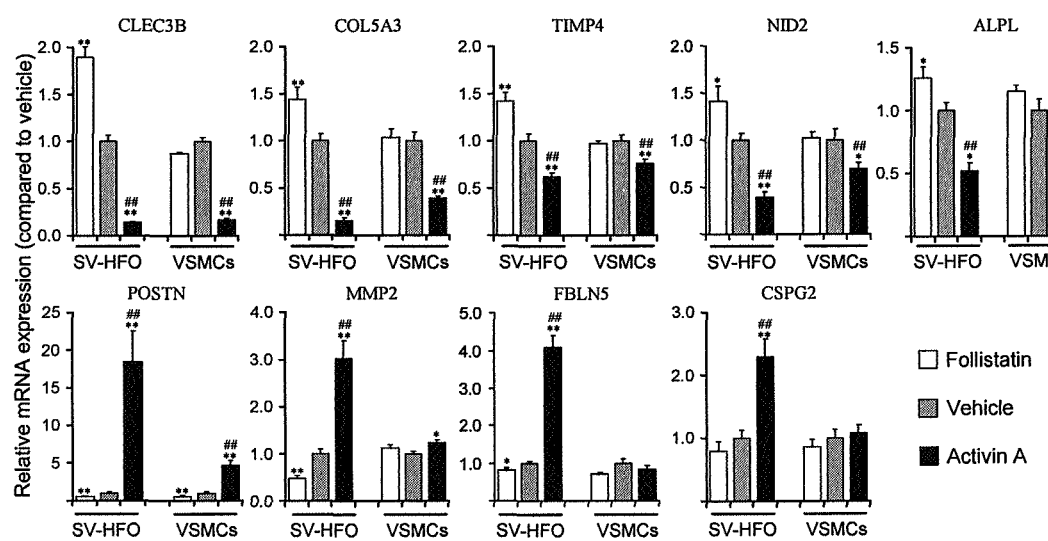
FIG. 9 shows the expression of genes localized in the extracellular matrix that are regulated by Activin-signaling in osteoblasts (SV-HFO) and vascular smooth muscle cells (VSMCs). QPCR analysis of a several selected ECM genes shown in FIG. 8 together with ALPL as a positive control. Expression was measured in activin-A- and follistatin-treated osteoblasts (SV-HFO, day 7) and VSMCs (day 12) cultures. The mRNA expression in vehicle cultures was set to 1 and used as a reference. * $p<0.05$; ** $p<0.01$ compared to vehicle. #$p<0.05$; ##$p<0.01$ compared to follistatin.

A selection of ECM genes was analyzed in more detail using qPCR in follistatin-, vehicle- and activin-treated osteoblasts together with their expression in VSMCs (FIG. 9). The expression of ALPL was also quantified as a positive control. This showed that CLEC3B, COL5A3, TIMP4, NID2 and ALPL, which were suppressed by activin-A (upper 5 panels) in osteoblasts were also suppressed by activin-A in VSMC cultures. POSTN was increased strongly by activin-signaling in osteoblasts, which was also demonstrated in VSMCs. In contrast, activin-A increased MMP2, FBLN5 and VCAN expression in osteoblasts but de expression of these genes was unchanged in VSMCs.

Follistatin treatment did not alter gene expression in VSMCs. This fits with the expression data of the INHBA and INHBB subunits in VSMC, which were both low expressed (mRNA) compared to the expression in osteoblasts (data not shown). Moreover activin-A production by VSMCs cultures could not be detected (data not shown). In VSMCs only POSTN mRNA expression was regulated by follistatin (0.5-fold). This gene was strongly induced by activin-signaling and probably already activated by low concentrations of activins (FIG. 8).

These expression data indicates that endogenous or exogenous activin-signaling alters ECM composition in osteoblasts cultures as well as in VSMCs cultures, preventing mineralization of the ECM. Albeit that endogenous activin-signaling is less prominent in mineralizing VSMCs.

The invention claimed is:

1. A method of stimulating mineralization in an extracellular matrix by an osteoblast in a human subject comprising:
   administering to said subject an effective amount of an activin-A inhibitor protein that is not follistatin, or a pharmaceutical composition thereof, wherein the activin-A inhibitor protein prevents an interaction between activin-A and an activin receptor on an osteoblast, and wherein the osteoblast mineralizes the extracellular matrix.

2. The method of claim 1 wherein the activin receptor is a type-II activin receptor.

3. The method of claim 1 wherein said administering is by intravenous, intraperitoneal or intracapsular administration.

4. The method of claim 1 wherein said administering is by means of a pump or sustained release form.

5. The method of claim 1 wherein said administering results in local concentration of said activin-A inhibitor protein of about 50-500 ng/ml.

6. The method of claim 1 wherein said activin-A inhibitor protein is conjugated to a targeting agent.

* * * * *